US007429693B2

(12) United States Patent
Zheng et al.

(10) Patent No.: US 7,429,693 B2
(45) Date of Patent: Sep. 30, 2008

(54) METHOD FOR THE PRODUCTION OF PLANT SEED WITH MODIFIED FIBER CONTENT AND MODIFIED SEED COAT

(75) Inventors: Zhifu Zheng, Saskatoon (CA); Tina Uchacz, Saskatoon (CA); Janet Taylor, Saskatoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 329 days.

(21) Appl. No.: 10/470,264

(22) Filed: May 11, 2005

(65) Prior Publication Data

US 2006/0281898 A1    Dec. 14, 2006

(51) Int. Cl.
*A01H 5/00* (2006.01)
*C12N 5/14* (2006.01)
*C12N 15/82* (2006.01)
*C07H 21/04* (2006.01)

(52) U.S. Cl. .................... 800/295; 435/320.1; 435/419; 435/468; 536/24.5; 536/23.1; 800/286; 800/306

(58) Field of Classification Search ........................ None
See application file for complete search history.

(56) References Cited

FOREIGN PATENT DOCUMENTS

| EP | 1 031 577 | 11/2003 |
| WO | WO/9807836 | * 2/1998 |
| WO | 98/49889 | 11/1998 |

OTHER PUBLICATIONS

Elomaa et al. (Molecular Breeding, 2:41-50, 1996).*
Colliver et al. (Plant molecular Biology, 35:509-522, 1997).*
Kumar et al. (Mol. Gen. Genet. 241;440-446, 1993).*
Maniatis et al. (Molecular Cloning: A Laboratory Manual, Cold Spring Harbor Laboratory, 1982).*
Barcikowska, et al. 1997, Seed coat pigmentation—F2 yellow-seed forms of *Brassica juncea* Coss X *B. carinata* Braun. *Rosliny-Oleiste* 18: 1, 99-102.
Bechtold, et al., C.R. Acad. Sci. Paris Life Sciences, 316: 1194-1199 (1993).
Chen et al., 1997, Identification and chromosomal assignment of RAPD markers linked with a gene for seed colour in a *Brassica-campestris-alboglabra* addition line, *Hereditas-Landskrona*, 126: 2, 133-138.
Lamar B, et al., "Hypothetical 28.4 kDa Protein", Database EMBL 'Online', Oct. 1, 2000, Database accession No. Q9MOA7, XP002208157, abstract.
Li-JiaNa, et al., 1998, An initial study of the inheritance of seed colour in yellow-seeded rapeseed (*Brassica napus*) lines with different genetic backgrounds, *Chinese Journal of Oil Crop Sciences*, 20: 4, 16-19.

Meng-JinLing, et al., 1998, The production of yellow-seede *Brassica napus* (AACC) through crossing interspecific hybrids of *B. campestris* (AA) and *B. carinata* (BBCC) with *B. napus*. Euphytica, 103: 3, 329-333.
Morgan C. L., et al, "Influence of testa colour and seed size on storage product composition in *Brassica juncea*", Plant Varieties & Seeds, vol. 11, No. 2, Aug. 1998, pp. 73-81, XP001094539, ISSN: 0952-3863.
Qi-CunKou, et al., 1996, Studies on the transfer of yellow-seeded trait from *Brassica carinata* to *B. napus*, *Jiangsu Journal of Agricultural Sciences*, 12:2, 23-28.
Teutonico R. A., et al., "Mapping of RFLP and qualitative trait loci in *Brasscia rapa* and comparison to the linkage maps of *B. napus, B. oleracea*, and *Arabidopsis thaliana*", Theoretical and Applied Genetics, vol. 89, 1994, pp. 885-894, XP001098081, ISSN: 0040-5752.
Van Deynze, A. E., et al., 1995, The identification of restriction fragment length polymorphisms linked to seed colour genes in *Brassica napus*, Genome 38: 3, 534-542.
Vyvadilova et al., 1999, The use of doubled haploids to stabilize yellow-seededness in oilseed rape (*Brassica napus*), Czech Journal of Genetics and Plant Breeding, 35: 1, 7-9.
Wu-JiangSheng, et al., 1997, Study on a new germplasm resource of a dominant gene controlling yellow seed coat in *Brassica napus L.*, Journal of Huazhong Agricultural University., 16: 1, 26-28.
Wu-JiangSheng et al., 1998, A study on the inheritance of a yellow-seeded mutant of rapeseed (*Brassica napus L.*)., Chinese Journal of Oil CRop Sciences, 20: 3, 6-9.
Zheng Zhifu, et al., "Isolation and characterization of novel defence-related genes induced by copper, salicyclic acid, methyl jasmonate, abscisic acid and pathogen infection in *Brassica carinata*", Molecular Plant Pathology, vol. 2, No. 3, May 2001, pp. 159-169, XP002208156, ISSN: 1464-6722.
Chaudhary et al., Abstract, Transgenic *Brassica carinata* as a vehicle for the production of recombinant proteins in seeds, Plant Cell Reports, Jan. 1998, pp. 195-200, vol. 17, No. 3.
Vogt et al. Abstract, Purification and Characterization of Sinapine Synthase from Seeds of *Brassica napus*, Archives of Biochemistry and Biophysics, feb. 1, 1993, pp. 622-28, vol. 300, No. 2.

* cited by examiner

*Primary Examiner*—Phuong Bui
*Assistant Examiner*—Vinod Kumar
(74) *Attorney, Agent, or Firm*—TraskBritt

(57) ABSTRACT

The present invention relates to a nucleotide sequences commonly designated CJAS1 comprising a novel gene from plants. The novel gene encodes a protein that is involved in seed formation and is associated with plant defense. The invention further relates to the use of the nucleotide sequence in the sense or antisense orientation to inhibit the expression of the plant gene corresponding to the CJAS1 sequence as a means to alter seed metabolism in plants, particularly cruciferous plants, more particularly *Brassica* species, to generate seeds with reduced fiber content and/or altered seed coats. The invention also relates to similar genes expressed in other plant species.

11 Claims, 7 Drawing Sheets

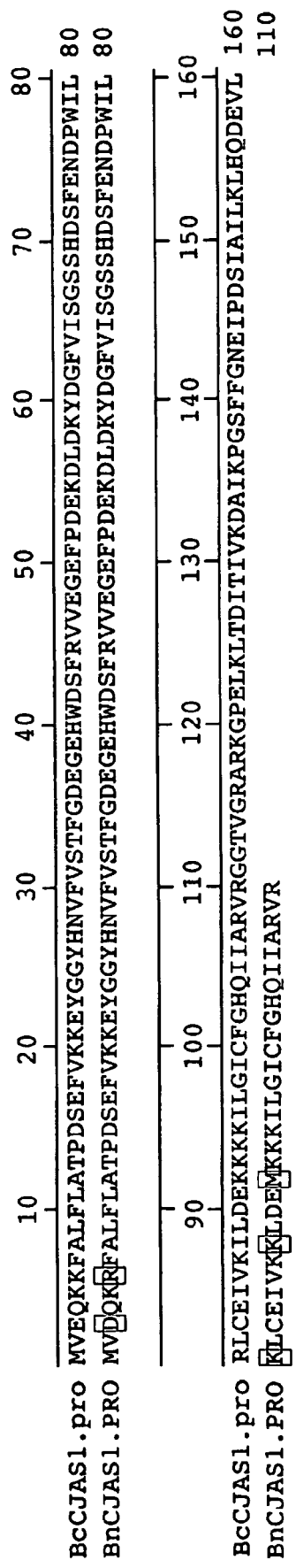

Figure 1:
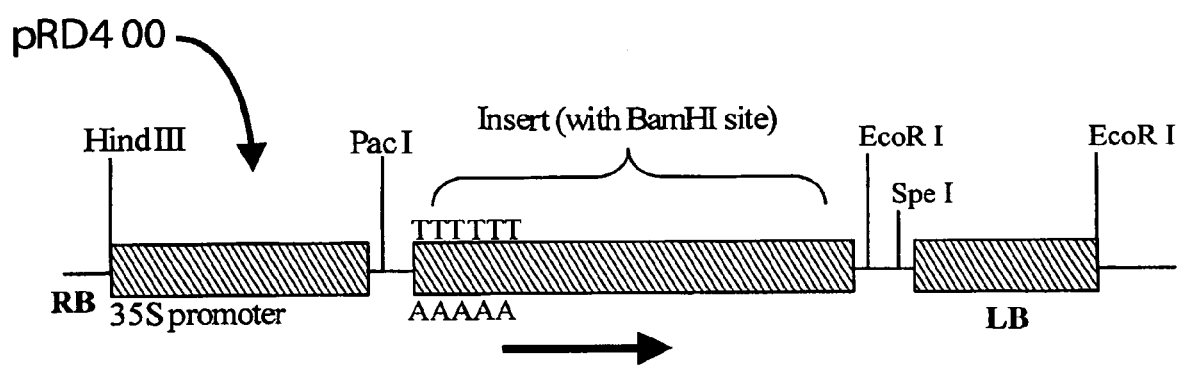

```
Majority         MV---EQKRFALFLATPDSEFVKKTYGGYHNVFVSTFGDEGEQWDLFRVVDGEFPDEKDLDKYDGFVISG
                         10         20         30         40         50         60         70

At2g23960-PRO    MV---EQKRFALFLATPDSEFVKKTYGGYHNVFVSTFGDEGEQWDLFRVVDGEFPDEKDLDKYEGFVISG  67
At2g23970-PRO    MA---EQKKYLLFLATPDSEFAKKTYGGYHNVFVSLLGDEGEQWDLFRVVDGEFPEEKDLEKYEGFVISG  68
At4g30530-pro    MV---NEQKRFALFLATSDSTFVKKAYGGYFNVFVSTFGLDGEQWDLFRVIDGEFPDDKDLDKYDGFVISG  67
At4g30540-pro    MV---EQKRYALFLATLDSEFVKKTYGGYHNVFVTTFGDEGEHWDSFRVVSGEFPDEKDLEKYDGFVISG  68
At4g30550-pro    M--VKQIIRYALFQATPDSEFVKEMYGGYFNVFVSAFGDEGEQWDLFRVIDGEFPRDEDLEKYEGFVISG  68
BcCJAS1-pro      MVVIEQKKRFALFLATCDSEFVKKTYGGYFNVFVSTFGEEGEQWDLFRVIDGQFPDENDLDKYDGFVISG  70
                 MV---EQKKFALFLATPDSEFVKKEYGGYHNVFVSTFGDEGEEWDSFRVVEGEFPDEKDLDKYDGFVISG  67

Majority         SSHDAFGDDDWILKLCSICKKLDDMKKKVVLGICFGHQIIARVKGGKVGRARKGPDLGLGSITIVKDAIKP
                         80         90        100        110        120        130        140

At2g23960-PRO    SSHDAFQDTDWILKLCLDIIKKLDDMNKKVVLGICFGHQLIARAKGGKVARARKGPELCLGNITIVKEAVMP  137
At2g23970-PRO    SLNDAFGDDDWIVKLCSLCDKLDDMKKKVVLGICFGHQILSRIKGGKVGRASRGLDMGLFSITMVFDAVKP  138
At4g30530-pro    SSHDAFENDDWILKLCDIVKKIDEMKKKILGICFGHQIIARVFGGFVGRAKKGPLLKLGDITIVKDAITP  137
At4g30540-pro    SLHDAFFEEDWIIELCSVCKKLDVMKKKILGICFGHQIICRVFGGKVGRARKGPDIGLGNITIVDDVIKP  138
At4g30550-pro    SFHDAFGDADWIVKLSEVCDKLDHMKKVVLGICFGHQIITRVKGGKIGRALKGADMGLFSITIAKDNEKL  140
BcCJAS1-pro      SSHDSFENDPWILRLCEIVKILDEKKKKILGICFGHQIIARVRGTVGRARKGPELKLTDITIVKDAIKP  137

Majority         GGYFGN-EIPASLAIIKCHQDEVLELPESAKVLAYSDKYEVEMFSIEDHLLCIQGHPEYNKEILFEIVDR
                        150        160        170        180        190        200        210

At2g23960-PRO    ENYFGE-EVPANLFIIKCHQDEVLIELPENAKLLAYSSMYEVEMYSIKDNFLCIQGHPEYNEDILFLIIDR  206
At2g23970-PRO    GGYFGS-QIPKSLAIIKCHQDEVLELPESATLLAYSDKYNVEMCSYGNHLLGIQGHPEYNKEILFEIIDR  207
At4g30530-pro    GSYFGN-EIPDSIAIIKCHQDEVLVLPETAKVLAYSKNYEVEMYSIEDHLFCIQGHPEYNKEILFEIVDR  206
At4g30540-pro    GDYFDQIE---SLSIIQCHFDEVLEFPESAFVIGFSDKCDVEIFSVEDHLLCFQGHPEYNKEILLEIIDR  205
At4g30550-pro    RGYFGDVEVPASLAIIKCHQDEVLELPESATLLASSEVCNVEMFSIGDHFFCIQGHPEYNKEILFEIVDR  210
BcCJAS1  -pro    GSFFGN-EIPDSIAILKLHQDEVLVLPESAKVLAYSEKYEVEMFSIEDHLFCIQGHPEYNDEILHEIVDR  206

Majority         VLALGLVEQEFADKAKATMENAGPDRKLWETLCKNFLKGRVPTN
                        220        230        240        250

At2g23960-Pro    VLAGGHIKVFF                                       217
At2g23970-Pro    VVNLKLMEQDFADKAKATMENAEPDRKQWQTLCKNFLKGRSEQV      251
At4g30530-pro    VLALGYVKQEFADAAKATMENRGADRKLWETICKNFLKGRVPTN      250
At4g30540-pro    VHKIKFVEEILLKAKDSIKKFLPDFQPLHMLCKNFLKGR-PTH       248
At4g30550-pro    VLMMKLMEQEFADKAKSTMETAQPDRILWQKLCKNFLKG           249
BcCJAS1  -pro    VLRLGFIKEDFADAAKASMENRGADRKLLETICKNFLKGRVPAN      250
```

FIG.8

```
SEQUENCE LISTING

<160> NUMBER OF SEQ ID NOS: 10

<210> SEQ ID NO 1
<211> LENGTH: 1044
<212> TYPE: DNA
<213> ORGANISM: Brassica carinata
<220> FEATURE:
<221> NAME/KEY: CDS
<222> LOCATION: (71)..(823)
<223> OTHER INFORMATION:

<400> SEQUENCE: 1
attgcacctc tctctttatt ctctctctgc taatcaacca ctctctctat ttacgttagc        60
cggtaaaaaa atg gtt gag cag aaa aag ttc gct ctg ttt cta gcg act       109
            Met Val Glu Gln Lys Lys Phe Ala Leu Phe Leu Ala Thr
            1               5                   10 cct gat tca gag ttc gtg aag aaa gag tac gga gga tac cac aac gtg       157
Pro Asp Ser Glu Phe Val Lys Lys Glu Tyr Gly Gly Tyr His Asn Val
    15                  20                  25 ttc gtg tcc acg ttc ggt gac gaa gga gag cat tgg gac tcg ttt aga       205
Phe Val Ser Thr Phe Gly Asp Glu Gly Glu His Trp Asp Ser Phe Arg
30                  35                  40                  45 gtc gtt gaa ggc gag ttt ccc gac gag aaa gat ctt gac aag tac gac       253
Val Val Glu Gly Glu Phe Pro Asp Glu Lys Asp Leu Asp Lys Tyr Asp
                50                  55                  60 ggt ttc gtt att agt gga agc tct cac gat tcc ttc gag aat gat cct       301
Gly Phe Val Ile Ser Gly Ser Ser His Asp Ser Phe Glu Asn Asp Pro
            65                  70                  75 tgg atc ctt agg cta tgt gag atc gtc aag ata ctc gat gag aag aag       349
Trp Ile Leu Arg Leu Cys Glu Ile Val Lys Ile Leu Asp Glu Lys Lys
        80                  85                  90 aag aaa att ctt ggc ata tgc ttt ggt cac cag atc ata gcc aga gta       397
Lys Lys Ile Leu Gly Ile Cys Phe Gly His Gln Ile Ile Ala Arg Val
    95                  100                 105 aga gga gga aca gtg gga aga gca agg aag gga cca gaa ctt aag ctt       445
Arg Gly Gly Thr Val Gly Arg Ala Arg Lys Gly Pro Glu Leu Lys Leu
110                 115                 120                 125 aca gac ata acc atc gtg aag gat gcg att aaa cca gga agt ttc ttc       493
Thr Asp Ile Thr Ile Val Lys Asp Ala Ile Lys Pro Gly Ser Phe Phe
                130                 135                 140 gga aac gag att ccg gat agc ata gcc atc cta aag tta cat cag gac       541
Gly Asn Glu Ile Pro Asp Ser Ile Ala Ile Leu Lys Leu His Gln Asp
```

-continued

```
                    145                 150                 155
gaa gtg tta gtg ttg cct gaa tct gct aaa gta cta gct tat tca gaa      589
Glu Val Leu Val Leu Pro Glu Ser Ala Lys Val Leu Ala Tyr Ser Glu
        160                 165                 170 aag tac gag gtg gag atg ttc tcc att gag gat cat tta ttc tgt att      637
Lys Tyr Glu Val Glu Met Phe Ser Ile Glu Asp His Leu Phe Cys Ile
    175                 180                 185 caa gga cat ccc gag tat aac aga gag att ctc cac gag atc gtt gat      685
Gln Gly His Pro Glu Tyr Asn Arg Glu Ile Leu His Glu Ile Val Asp
190                 195                 200                 205 cgt gtt ctt cgt ctt ggc ttc atc aag gaa gat ttt gcg gat gcg gca      733
Arg Val Leu Arg Leu Gly Phe Ile Lys Glu Asp Phe Ala Asp Ala Ala
                210                 215                 220 aaa gcc tcg atg gag aat agg gga gca gac agg aaa ctt ttg gag acg      781
Lys Ala Ser Met Glu Asn Arg Gly Ala Asp Arg Lys Leu Leu Glu Thr
            225                 230                 235 att tgc aag aat ttt ctc aaa ggc aga gtt cca gct aat taa              823
Ile Cys Lys Asn Phe Leu Lys Gly Arg Val Pro Ala Asn
        240                 245                 250 ttagtttcac tcccaaatta tctatttggc tcttgttata ttggagctag cacttatgga    883
tttattatct tgctgtattg tattcaatat ataacctatt aatctcatcc ttgtcaagga    943
aacaaaaact catattaatc tcaatgtcat atttatgtgt tgttacccat aagtaaaatt    1003
attcaataaa aactatagtt ttgcaaaaaa aaaaaaaaaa a                        1044
```

<210> SEQ ID NO 2
<211> LENGTH: 250
<212> TYPE: PRT
<213> ORGANISM: Brassica carinata

<400> SEQUENCE: 2

```
Met Val Glu Gln Lys Lys Phe Ala Leu Phe Leu Ala Thr Pro Asp Ser
1               5                   10                  15

Glu Phe Val Lys Lys Glu Tyr Gly Gly Tyr His Asn Val Phe Val Ser
            20                  25                  30

Thr Phe Gly Asp Glu Gly Glu His Trp Asp Ser Phe Arg Val Val Glu
        35                  40                  45

Gly Glu Phe Pro Asp Glu Lys Asp Leu Asp Lys Tyr Asp Gly Phe Val
    50                  55                  60

Ile Ser Gly Ser His Asp Ser Phe Glu Asn Asp Pro Trp Ile Leu
65              70                  75                  80

Arg Leu Cys Glu Ile Val Lys Ile Leu Asp Glu Lys Lys Lys Ile
            85                  90                  95

Leu Gly Ile Cys Phe Gly His Gln Ile Ile Ala Arg Val Arg Gly Gly
        100                 105                 110

Thr Val Gly Arg Ala Arg Lys Gly Pro Glu Leu Lys Leu Thr Asp Ile
    115                 120                 125

Thr Ile Val Lys Asp Ala Ile Lys Pro Gly Ser Phe Phe Gly Asn Glu
130                 135                 140

Ile Pro Asp Ser Ile Ala Ile Leu Lys Leu His Gln Asp Glu Val Leu
145                 150                 155                 160

Val Leu Pro Glu Ser Ala Lys Val Leu Ala Tyr Ser Glu Lys Tyr Glu
            165                 170                 175

Val Glu Met Phe Ser Ile Glu Asp His Leu Phe Cys Ile Gln Gly His
        180                 185                 190

Pro Glu Tyr Asn Arg Glu Ile Leu His Glu Ile Val Asp Arg Val Leu
```

-continued

```
                195                 200                 205
Arg Leu Gly Phe Ile Lys Glu Asp Phe Ala Asp Ala Lys Ala Ser
    210                 215                 220
Met Glu Asn Arg Gly Ala Asp Arg Lys Leu Leu Glu Thr Ile Cys Lys
225                 230                 235                 240
Asn Phe Leu Lys Gly Arg Val Pro Ala Asn
                245                 250

<210> SEQ ID NO 3
<211> LENGTH: 1006
<212> TYPE: DNA
<213> ORGANISM: Brassica napus
<220> FEATURE:
<221> NAME/KEY: CDS
<222> LOCATION: (75)..(827)
<223> OTHER INFORMATION:

<400> SEQUENCE: 3
attgcacctc tatctctgtt atctctttct ctctcttcta atcaaccact ctccctattt      60
tctttagccg aaaa atg gtt gat cag aaa agg ttt gca ctg ttt ctt gca      110
              Met Val Asp Gln Lys Arg Phe Ala Leu Phe Leu Ala
                1               5                  10 act cct gat tca gag ttc gta aag aaa gag tac ggt gga tac cat aac      158
Thr Pro Asp Ser Glu Phe Val Lys Lys Glu Tyr Gly Gly Tyr His Asn
         15                  20                  25 gtg ttt gtc tcc acg ttc gga gac gaa gga gag cat tgg gac tcg ttt      206
Val Phe Val Ser Thr Phe Gly Asp Glu Gly Glu His Trp Asp Ser Phe
     30                  35                  40 aga gtc gta gag ggc gag ttt ccc gat gag aaa gat ctt gac aag tac      254
Arg Val Val Glu Gly Glu Phe Pro Asp Glu Lys Asp Leu Asp Lys Tyr
 45                  50                  55                  60 gat ggt ttc gtt att agc gga agc tct cac gat tcc ttc gag aat gat      302
Asp Gly Phe Val Ile Ser Gly Ser Ser His Asp Ser Phe Glu Asn Asp
                 65                  70                  75 cct tgg atc ctt aag cta tgt gag atc gtc aag aaa ctt gat gag atg      350
Pro Trp Ile Leu Lys Leu Cys Glu Ile Val Lys Lys Leu Asp Glu Met
             80                  85                  90 aag aag aag att ctt ggc atc tgc ttt ggt cac cag atc ata gcc aga      398
Lys Lys Lys Ile Leu Gly Ile Cys Phe Gly His Gln Ile Ile Ala Arg
         95                  100                 105 gta aga gga ggg aca gtg gga aga gca agg aaa gga ccc gaa ctt aag      446
Val Arg Gly Gly Thr Val Gly Arg Ala Arg Lys Gly Pro Glu Leu Lys
    110                 115                 120 ctt aca gac ata gcc atc gtg aag gat gcg att aaa ccg gga agt ttc      494
Leu Thr Asp Ile Ala Ile Val Lys Asp Ala Ile Lys Pro Gly Ser Phe
125                 130                 135                 140 ttc gga aac gag att ccg gat agc ata gcc atc cta aag tta cat cag      542
Phe Gly Asn Glu Ile Pro Asp Ser Ile Ala Ile Leu Lys Leu His Gln
                145                 150                 155 gac gaa gtt tta gtg ttg cct gaa tct gct aaa gta cta gct ttt tcc      590
Asp Glu Val Leu Val Leu Pro Glu Ser Ala Lys Val Leu Ala Phe Ser
            160                 165                 170 gaa aag tac gag gtg gag atg ttc tcc att gag gat cat tta ttc tgt      638
Glu Lys Tyr Glu Val Glu Met Phe Ser Ile Glu Asp His Leu Phe Cys
        175                 180                 185 att caa gga cat ccc gag tat aac aaa gag att ctc cac gag atc gtt      686
Ile Gln Gly His Pro Glu Tyr Asn Lys Glu Ile Leu His Glu Ile Val
    190                 195                 200 gat cgt gtt ctt cgt ctt ggc ttc atc aag caa gat ttt gcg gat gcg      734
Asp Arg Val Leu Arg Leu Gly Phe Ile Lys Gln Asp Phe Ala Asp Ala
```

```
gca aag gcc tcg atg gag aat agg gga gca gac agg aaa ctc ttg gag      782
Ala Lys Ala Ser Met Glu Asn Arg Gly Ala Asp Arg Lys Leu Leu Glu
            225                 230                 235 acg att tgc aag aat ttc ctc aaa ggc aga gtt cca gct aat taa           827
Thr Ile Cys Lys Asn Phe Leu Lys Gly Arg Val Pro Ala Asn
        240                 245                 250 ttagtttctc tcccaaatta tctatttggc tcttgttata tctgagcact tatagattta     887
tcatcttgct gtattcttat tcaatatata acctattatt ctcatccttg tcaggaaaac     947
aaaaactcat attaatctca atgtcacatt tatgtaaaaa aaaaaaaaaa aaaaaaaa      1006

<210> SEQ ID NO 4
<211> LENGTH: 250
<212> TYPE: PRT
<213> ORGANISM: Brassica napus

<400> SEQUENCE: 4

Met Val Asp Gln Lys Arg Phe Ala Leu Phe Leu Ala Thr Pro Asp Ser
1               5                   10                  15

Glu Phe Val Lys Lys Glu Tyr Gly Gly Tyr His Asn Val Phe Val Ser
            20                  25                  30

Thr Phe Gly Asp Glu Gly Glu His Trp Asp Ser Phe Arg Val Val Glu
        35                  40                  45

Gly Glu Phe Pro Asp Glu Lys Asp Leu Asp Lys Tyr Asp Gly Phe Val
    50                  55                  60

Ile Ser Gly Ser Ser His Asp Ser Phe Glu Asn Asp Pro Trp Ile Leu
65                  70                  75                  80

Lys Leu Cys Glu Ile Val Lys Lys Leu Asp Glu Met Lys Lys Lys Ile
                85                  90                  95

Leu Gly Ile Cys Phe Gly His Gln Ile Ile Ala Arg Val Arg Gly Gly
            100                 105                 110

Thr Val Gly Arg Ala Arg Lys Gly Pro Glu Leu Lys Leu Thr Asp Ile
        115                 120                 125

Ala Ile Val Lys Asp Ala Ile Lys Pro Gly Ser Phe Phe Gly Asn Glu
    130                 135                 140

Ile Pro Asp Ser Ile Ala Ile Leu Lys Leu His Gln Asp Glu Val Leu
145                 150                 155                 160

Val Leu Pro Glu Ser Ala Lys Val Leu Ala Phe Ser Glu Lys Tyr Glu
                165                 170                 175

Val Glu Met Phe Ser Ile Glu Asp His Leu Phe Cys Ile Gln Gly His
            180                 185                 190

Pro Glu Tyr Asn Lys Glu Ile Leu His Glu Ile Val Asp Arg Val Leu
        195                 200                 205

Arg Leu Gly Phe Ile Lys Gln Asp Phe Ala Asp Ala Ala Lys Ala Ser
    210                 215                 220

Met Glu Asn Arg Gly Ala Asp Arg Lys Leu Leu Glu Thr Ile Cys Lys
225                 230                 235                 240

Asn Phe Leu Lys Gly Arg Val Pro Ala Asn
                245                 250

<210> SEQ ID NO 5
<211> LENGTH: 275
<212> TYPE: DNA
<213> ORGANISM: Brassica napus

<400> SEQUENCE: 5
```

-continued

```
caaaagaagt acctattgtt tcacaaataa tatataggggg atcaatgata ttatacaaga    60
cgagaattgg tacgataaaa attataacag cttacagatt acagaacaca aattgtaccc   120
tcaagcgatg acttagaaag agttatctca gttgatgatg aaacttgtat aaattcaact   180
atcaataatg aaaggtagct atcaaaatta aatatcaaaa gttctttgaa actagaaatt   240
caaaatttca cacttactag tccacatgat gcttt                              275
```

<210> SEQ ID NO 6
<211> LENGTH: 25
<212> TYPE: DNA
<213> ORGANISM: Artificial sequence
<220> FEATURE:
<223> OTHER INFORMATION: TW1 primer

<400> SEQUENCE: 6

```
ccttcacgat ggttatgtct gtaag                                          25
```

<210> SEQ ID NO 7
<211> LENGTH: 28
<212> TYPE: DNA
<213> ORGANISM: Artificial sequence
<220> FEATURE:
<223> OTHER INFORMATION: TW2 primer

<400> SEQUENCE: 7

```
ctcttactct ggctatgatc tggtgacc                                       28
```

<210> SEQ ID NO 8
<211> LENGTH: 27
<212> TYPE: DNA
<213> ORGANISM: Artificial sequence
<220> FEATURE:
<223> OTHER INFORMATION: TW8 primer

<400> SEQUENCE: 8

```
attgcacctc tatctctgtt atctctt                                        27
```

<210> SEQ ID NO 9
<211> LENGTH: 21
<212> TYPE: DNA
<213> ORGANISM: Artificial sequence
<220> FEATURE:
<223> OTHER INFORMATION: TW10 primer

<400> SEQUENCE: 9

```
caaaagaagt acctattgtt t                                              21
```

<210> SEQ ID NO 10
<211> LENGTH: 18
<212> TYPE: DNA
<213> ORGANISM: Artificial sequence
<220> FEATURE:
<223> OTHER INFORMATION: TW12 primer

<400> SEQUENCE: 10

```
aaagcatcat gtggacta                                                  18
```

METHOD FOR THE PRODUCTION OF PLANT SEED WITH MODIFIED FIBER CONTENT AND MODIFIED SEED COAT

1. FIELD OF THE INVENTION

The present invention relates to plant genes involved in the formation of the seed coat in plants and in the fibre content of seeds. In particular, the present invention relates to plant genes involved in the formation of seed coat and the fibre content of seeds from *Brassica* and other species.

2. BACKGROUND OF THE INVENTION

Plant seeds contain a number of different tissues including the embryo and cotyledons that are usually encased in a layer of thickened and lignified tissue referred to as a seed coat. In general, seed coats contain a significant portion of the total undigestable fibre content of plant seeds. Plant seeds with reduced fibre content provide many advantages for use as feed products. Thus, alteration of the seed coat composition, as well as alteration of the composition of the other tissues of the seed for reduced fibre content can provide an improvement for plant seeds currently used for feed.

The seed coat provides a mechanical barrier that protects the seed prior to germination and allows the seed to remain dormant or withstand mechanical challenges. Some plant species have extremely strong seed coats that can withstand significant mechanical and environmental insult. Other plant species have thinner seed coats that offer a limited degree of protection from mechanical damage. The nature of the seed coat is determined genetically and is typically correlated with the biology and ecology of the plant species.

In many crop species of commercial interest, a thick seed coat is generally undesirable since the seed coat tends to contain a high level of undigestible fibre and is often a waste product upon processing of the seed for oil, meal or other products. The seed coat contributes a significant portion of the fibre content to plant seed meals. Thus, reduction of the seed coat is an important goal for crop improvement in many crop species. However the importance of the seed coat for the protection of the seed itself dictates that any reduction in seed coat still allow for the protection of the seed from injury or damage during seed harvesting, processing, or planting of seed. Accordingly a balance between seed coat size and composition and the mechanical barrier function the seed coat provides must be achieved.

The composition of the seed coat (or hull) is also a consideration for improvement in many crop species, particularly those that are used for feed. Fibre content of meals derived from plant seed is an important consideration for formulation of rations. Fibre levels of feed products must be carefully maintained for many applications since high levels of dietary fibre are associated with poor utilization of the meal and in some cases limits the utility of the meal. The plant cell wall constitutes the majority of dietary fibre and this fibre is composed of a relatively limited number of starting compounds arranged in a large number of different final products. The matrix of the cell walls contains most of the fibre component and this fibre is composed of various polymers in both covalent and non-covalent bonds.

Examples of covalent "fibre" bonds include esterified cross-linked sugar residues such as those found in pectins and non-cellulose polysaccharides and cross linked lignin and extensin molecules. Non-covalent "fibre" bonds include associations in cellulose fibres and $Ca^{++}$ ion bridges between pectins. The cell walls and associated "fibre" component of *Brassica* seeds include primary cells walls and some specialized types. Seeds consist of three main parts, cotyledons, embryo axis and reserve tissues. Cotyledons are generally thin-walled parenchema cells in contrast to the pericarp and testa which contain thickened, lignified and suberized cell walls embedded with various undigestable compounds. Accordingly the dehulling approach has an obvious advantage in the physical separation of the portions of the seed high in fibre. Although the hull is a relatively small portion of the seed on a weight basis, it does contain a significant amount of the fibre content of seeds, but further reductions in fibre content would be desirable.

Unfortunately, the precise biochemical composition of the fibre component of each of the cell types in plants has not been carried out. Therefore all "fibre" content figures tend to be generalizations and may not accurately reflect the actual composition of the fibre component. At the most simple and general level, plant cell walls or fibre is composed primarily of four complex compounds. These are cellulose, non-cellulose polysacharides, proteins and phenolic compounds or lignins. Cellulose is a simple compound comprised of repeating glucose residues, however the actual supramolecular structure of the molecule is complex. Non-cellulose polysaccharides are comprised of acid pectic polysaccharides, hemicelluloses and various polymers of structurally distinct sugars. There are a number of protein components to the fibre the largest portion of which is extensin, a unique protein that forms a backbone for the further cross linking of many compounds. Lignin of course represents the primary phenolic component. For the most part, none of these components are effectively utilized by monogastric animals in diets.

Fibre content in seeds and seed meal is generally expressed as crude fibre, acid detergent fibre or neutral detergent fibre. Crude fibre (CF) typically includes lignin, cellulosic, hemicellulosic and pectin fractions of the seed. Acid detergent fibre (ADF) typically includes cellulosic and acid stable lignin fractions, while neutral detergent fibre (NDF) tends to represent lignin, cellulose and hemicellulose components. Thus the term fibre can mean many different chemical components. The methods for determination of the levels of these various fibre components are standardized according to AOAC (Association of Official Agricultural Chemists) methods.

The digestability of seed meal is dependent on the composition of the fibre component. Some seed coats or hulls are highly lignified and generally resistant to degradation following ingestion while other seed coats may have a composition that allows easier degradation in the gut of an animal. Thus a seed coat that is low in fibre is an important objective for crop improvement. Similarly, the composition of a seed coat will influence the processing of seed for seed products such as protein, starch or oil, seed coats that are more amenable to processing are preferred. This may include seed coats with reduced level of pigments or seed coats with altered secondary metabolite composition.

Generally *Brassica* oilseed crops are processed for oil and meal by the use of crushing techniques. Oil is extracted from seed following the disruption of the seed and the resultant solid material is referred to as meal. Typically seed coats are found in the meal fraction, although it is possible to remove the seed coat (dehull the seed) before processing, removal of the hull is an additional cost and leads to additional waste products.

In *Brassica*, there are numerous types of oilseed varieties, including high erucic acid, rapeseed and canola quality varieties. Canola quality varieties are the most predominant types of oilseed *Brassica* species grown for edible oil. Canola quality refers to a specific oil composition with reduced glucosinolate and erucic acid content providing a highly valuable edible oil. *Brassica* varieties that produce high levels of erucic acid are grown for industrial purposes, and rapeseed lines are generally not used for edible oil production, except under certain instances or locations where the lower quality of rapeseed oil is tolerated by market conditions. Although rapeseed is widely grown, rapeseed oil does not command the premium seen for canola quality oil. Thus, canola quality varieties are of primary value to the industry.

Many *Brassica* species produce seed that typically has a dark seed coat, with a few species producing seed with a yellow seed coat. The normal black seed coat of canola quality oilseed *Brassica napus* imparts undesirable visual characteristics to both the oil and the meal of canola varieties upon typical processing of canola seed. Upon crushing of the canola seed, oil and meal fractions are isolated that are contaminated with seed coat or pigments found within the seed coat. The oil is dark during the initial stages of processing which makes it appear spoiled. In meal, the bits of black seed coat mixed with the light meal make it appear to be infested with insects. Thus a seed coat that is lighter in color can have advantages for the canola crushing industry.

Breeding canola quality *Brassica* seed with reduced seed coat has been an important objective for canola breeders. Some *Brassica* species have a seed coat that is yellow in color and it has been found that the yellow color is associated with a seed coat that is typically thinner and reduced in size. The yellow seed coat also appears to have reduced fibre and is likely more digestible due to the absence of certain pigments or secondary metabolites commonly associated with a dark, thicker, more lignified seed coat. Meal produced from yellow seeded species of *Brassica* will typically have less fibre and provide a product that has, on a percentage basis, higher protein content thus being more valuable. Accordingly, reduction of the size of the seed coat will carry many advantages. Thus the development of *Brassica napus* species with a yellow seed coat is an important goal for the *Brassica* oilseed industry.

Studies have been carried out with the objectives to find new sources of genes encoding the formation of a yellow seed coat in *Brassica*, for example: Wu-JiangSheng et al., 1997, Study on a new germplasm resource of a dominant gene controlling yellow seed coat in *Brassica napus* L., *Journal-of-Huazhong-Agricultural-University.*, 16: 1, 26-28., Wu-JiangSheng et al., 1998, A study on the inheritance of a yellow-seeded mutant of rapeseed (*Brassica napus* L.)., *Chinese-Journal-of-Oil-Crop-Sciences* 20: 3, 6-9., Li-JiaNa et al., 1998, An initial study of the inheritance of seed colour in yellow-seeded rapeseed (*Brassica napus*) lines with different genetic backgrounds. *Chinese-Journal-of-Oil-Crop-Sciences* 20: 4, 16-19. However, most of the traits identified are not suitable for simple introgression into canola quality *Brassica* breeding lines.

Other attempts to introduce a yellow seed coat into *Brassica napus* have included the introgression of the yellow seeded trait from other *Brassica* species that are being developed into edible oilseed quality breeding lines. Examples of these studies include: Barcikowska et al., 1997, Seed coat pigmentation—F2 yellow-seed forms of *Brassica juncea* Coss X *B. carinata* Braun. *Rosliny-Oleiste* 18: 1, 99-102., Meng-JinLing et al., 1998, The production of yellow-seeded *Brassica napus* (AACC) through crossing interspecific hybrids of *B. campestris* (AA) and *B. carinata* (BBCC) with *B. napus*. *Euphytica*. 103: 3, 329-333., Qi-CunKou et al., 1996, Studies on the transfer of yellow-seeded trait from *Brassica carinata* to *B. napus*. *Jiangsu-Journal-of-Agricultural-Sciences* 12: 2, 23-28. Although it is possible to obtain yellow seeded lines from these interspecific crosses, the resultant lines are often unstable with regards to the trait and stabilization and management of the trait during the breeding process often proves unreliable.

Accordingly, some experiments have been carried out to to provide a means to stabilize the trait e.g., Vyvadilova et al., 1999, The use of doubled haploids to stabilize yellow-seededness in oilseed rape (*Brassica napus*)., *Czech-Journal-of-Genetics-and-Plant-Breeding*. 35: 1, 7-9., but the ability to routinely stabilize and obtain yellow seeded varieties is not predictable or conveniently accomplished.

Still other work has been conducted to identify molecular markers that co-segregate with the yellow seeded trait as a means to more efficiently manage the production of yellow seeded *Brassica* varieties. These include: Chen-B Y et al., 1997, Identification and chromosomal assignment of RAPD markers linked with a gene for seed colour in a *Brassica campestris-alboglabra* addition line., *Hereditas-Landskrona* 126: 2, 133-138., and Deynze-A E-van, et al., 1995,The identification of restriction fragment length polymorphisms linked to seed colour genes in *Brassica napus.*, *Genome* 38: 3, 534-542.

Still other studies have attempted to select mutation in *Brassica* to impart the yellow seed color. WO9849889A1 teaches a method to select yellow seeded characteristics from rapeseed lines through the use of microspore culture and selection of mutated lines, but the resultant plants must be used for breeding into canola quality lines and this is a difficult and laborious process to carry out if the intent is to derive canola quality lines containing a yellow seed coat.

Despite all of these studies, a convenient source of a lower fibre, yellow seeded trait in *Brassica* or a convenient means to manipulate the naturally occurring trait in other *Brassica* species has yet to be identified. In addition, the development of yellow seeded varieties with low fibre content is a most preferred objective of many *Brassica* oilseed breeding programs. However, this has been difficult to accomplish to date. Thus, nearly all of the *Brassica napus* oilseed crops commercially grown still have the dark-seeded characteristic and only a few have varying degrees of yellow seeded characteristics. The fibre content of conventional canola varieties has remained more or less constant despite these efforts towards the production of low fibre, yellow seeded varieties. Thus, it remains an important objective for the *Brassica* oilseed industry to develop yellow seeded canola varieties.

Development of a means to reduce fibre and manipulate seed coat color in related *Brassica* species, including members of the cruciferous family can open the possibility of developing canola quality crop species from those species where seed coat color and characteristics are undesireable. Therefore the ability to develop crops, and in particular cruciferous crops, with reduced fibre and altered seed coats is an important element in the further development of new oilseed and meal crops.

3. SUMMARY OF THE INVENTION

It is an object of the present invention to provide a polynucleotide sequence encoding a protein involved in the formation of fibre in plant seeds.

It is a further object of the present invention to provide a polynucleotide sequence encoding a protein involved in the formation of the seed coat of plant seeds.

It is a further object of the present invention to provide a method of modifying a plant to reduce the fibre content of the seeds of the plant.

It is a further object of the present invention to provide a method of modifying a plant to alter the colour of the seeds of the plant.

It is a further object of the present invention to generate a transgenic plant with a reduced fibre content compared to the unmodified plant.

It is a further object of the present invention to generate a transgenic plant with an altered seed colour compared to the unmodified plant.

In one aspect, the present invention provides nucleic acid sequences encoding proteins involved in the formation of typical high fibre, dark colored seed coats in *Brassica* and cruciferous species. The nucleic acids of the present invention, when expressed in an antisense orientation relative to the normal presentation can cause the reduction of fibre content, and the formation of yellow colored seed coats in *Brassica* varieties that normally have dark seed coats. Moreover, the nucleic acid sequences of the present invention may be expressed in other plant varieties to achieve similar results.

The present invention also provides for polynucleotide sequences involved in the control of fibre content in plant seed. When the polynucleotide sequences of the present invention are expressed in plants in an antisense orientation relative to the normal presentation, seeds are generated with reduced crude fibre content relative to seeds from varieties with dark seed coats.

In one aspect, the present invention provides an isolated nucleotide sequence characterized in that the isolated nucleotide is selected from:
a) SEQ ID NO: 1, or a complement thereof,
b) SEQ ID NO: 3, or a complement thereof,
c) a nucleotide sequence encoding a peptide with at least 50%, preferably 70%, more preferably 90%, most preferably 95% homology to a peptide encoded by the nucleotide sequence of a) or b);

wherein said isolated nucleotide sequence or complement thereof encodes a protein or a part thereof, that alters seed development in a plant expressing said nucleotide sequence.

In another aspect, the present invention provides an isolated nucleotide sequence characterized in that the isolated nucleotide sequence is selected from:
a) SEQ ID NO: 1, or a complement thereof;
b) SEQ ID NO: 3, or a complement thereof; and
c) a nucleotide sequence that hybridizes under stringent conditions (65° C., 6×SSC) to a) or b);

wherein said isolated nucleotide sequence or complement thereof encodes a protein or part thereof, that alters seed development in a plant expressing said nucleotide sequence.

Preferably, the nucleotide sequences of the present invention are derived from a cruciferous plant or a plant of the genus *Brassica*.

Preferably, the nucleotide sequence of the present invention is characterized in that expression of the nucleotide sequence in a plant reduces the fibre content of the seeds, and/or lightens the colour of the seeds of the plant, when compared to the seeds of an unmodified plant.

The present invention also encompasses isolated and purified peptides characterized in that the peptides are encoded by the nucleotide sequences of the invention.

In other aspects, the nucleotide sequences of the present invention may be utilized for the generation of DNA expression cassettes, or constructs comprising a nucleotide sequence operably linked to a promoter.

In further aspects, the present invention encompasses plant cells characterized in that the plant cells are transformed with the aforementioned constructs, as well as transgenic plants derived from regeneration of the transformed plants cells into whole plants. In preferred embodiments, the transgenic plants of the present invention are cruciferous plants, or plants of the genus *Brassica*.

In alternative embodiments, the present invention also provides for a method for modifying the seed of a plant characterized in that the method comprises the steps of:
(a) introducing into a plant cell capable of being transformed and regenerated into a whole plant a construct comprising, in addition to the DNA sequences required for transformation and selection in plants, a nucleotide sequence in accordance with the present invention, operably linked to a promoter; and
(b) recovery of a plant which contains the nucleotide sequence. Most preferably, the method generates plants bearing seeds with reduced fibre content and/or a lightened colour when compared to seeds from a normal plant. In other aspects, the method may involve the use of constructs comprising sense or antisense orientation of the nucleotide sequences of the present invention, relative to the promoter.

The present invention also encompasses seeds characterized in that the seeds are obtained from the transgenic plants and corresponding methods disclosed herein.

In particular aspects, the present invention discloses the homologous nucleotide sequences designated SEQ ID NO:1, 3, and 5 in the sequence listing. For the purposes of the present disclosure, these sequences are collectively termed CJAS1.

The present invention provides for the transformation of plants using the CJAS1 sequences disclosed, and homologues thereof. The seed of a plant can be modified by the transformation of plant cells with a plant transformation vector comprising a sense or antisense portion of the CJAS1 sequence or a double stranded RNA comprising both sense and antisense portions of the gene.

The CJAS1 sequence may also be used for identification of related homologous sequences deposited in public databases through comparative techniques well-known in the art, or for the generation of a hybridization probe for the identification of related cDNA or genomic sequences from various plant species.

The present invention further provides a method of identifying and isolating a DNA sequence substantially homologous to the nucleotide sequences disclosed in the present application, characterized in that the method comprises the steps of:
synthesizing a degenerate oligonucleotide primer than can hybridize to a nucleotide sequence disclosed herein under stringent conditions;
labelling said degenerate oligonucleotide primer; and
using said labelled degenerate oligonucleotide primer as a probe to screen a DNA library for said substantially homologous DNA sequence.

The present invention also provides for the use of an isolated nucleotide sequence according encompassed by the invention, for generating a transgenic plant having seeds with a reduced fibre content and/or with a lighter colour when compared to seeds of an unmodified plant.

4. BRIEF DESCRIPTION OF THE DRAWINGS

FIG. 1: Plant transformation vector comprising the CJAS1 cDNA. The arrow indicates the direction of antisense expression from the 35S promoter.

Figure 2A:
Figure 2B:

FIG. 2*a*: seeds from wild-type *Brassica carinata*, and FIG. 2*b*: seeds obtained from transgenic *Brassica carinata* expressing CJAS1 (SEQ ID NO: 1) in an antisense orientation.

Figure 3:
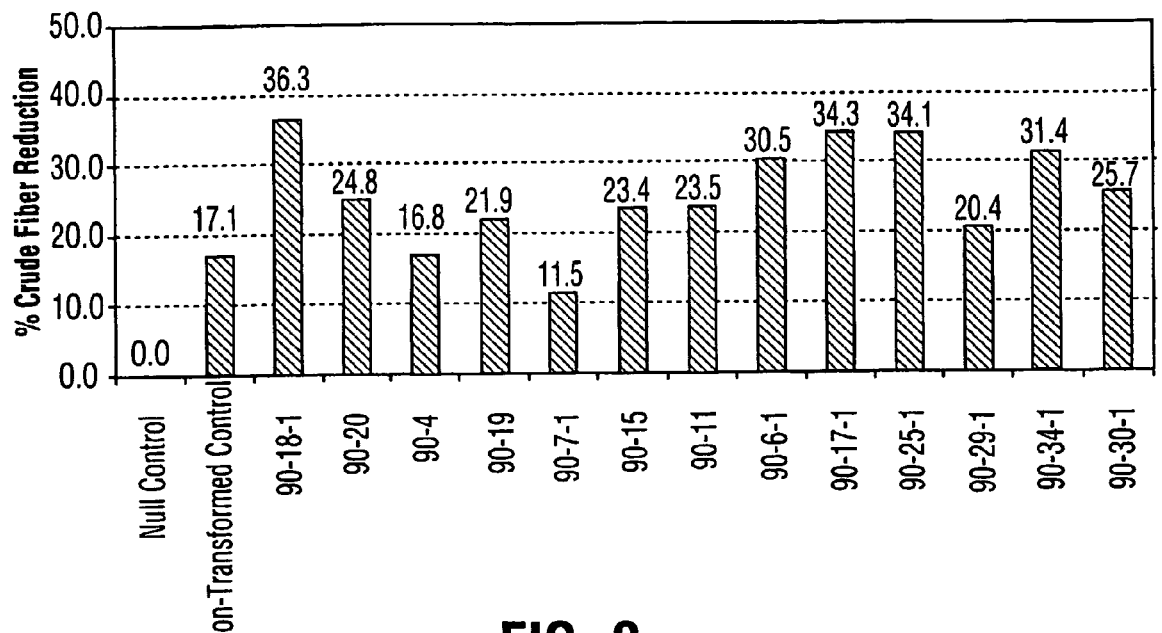

FIG. 3: Graphic representation of the reduction of crude fibre in transgenic *Brassica*.

Figure 4:
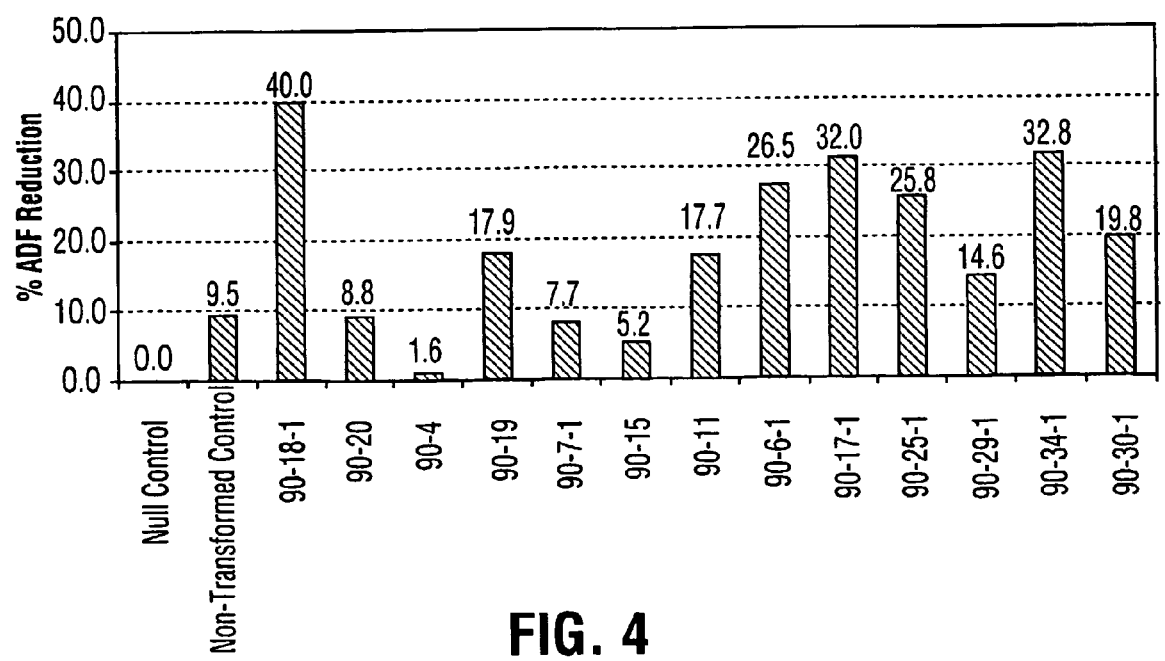

FIG. 4: Graphic representation of the reduction of acid detergent fibre in transgenic *Brassica*.

Figure 5:
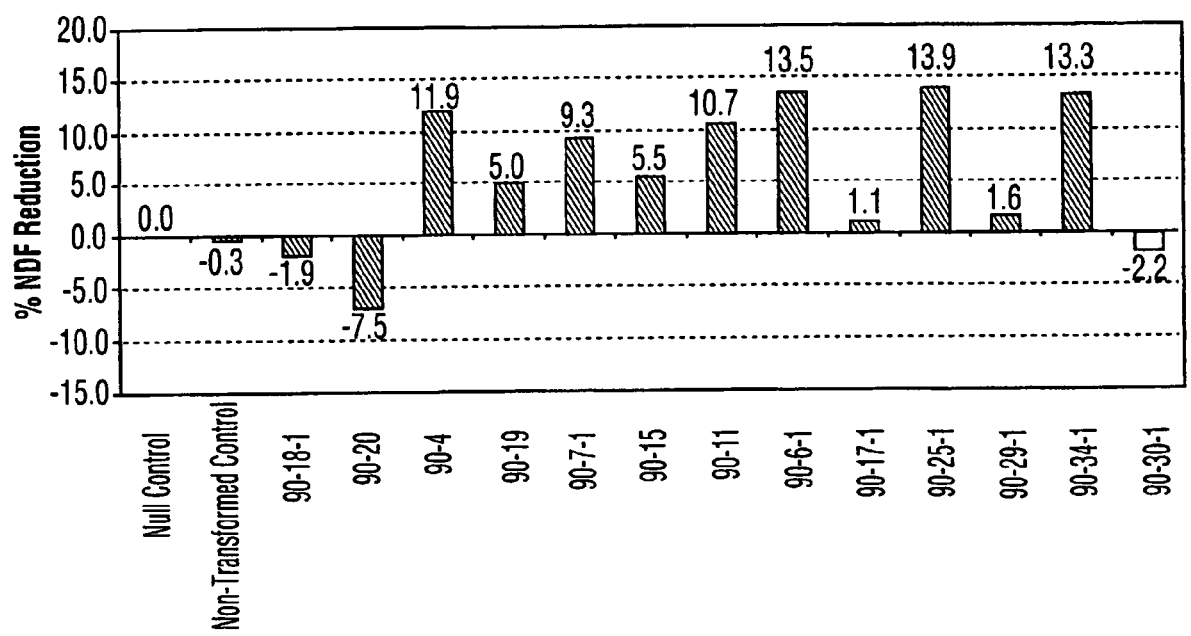

FIG. 5: Graphic representation of the reduction of neutral detergent fibre in transgenic *Brassica*.

Figure 6A:
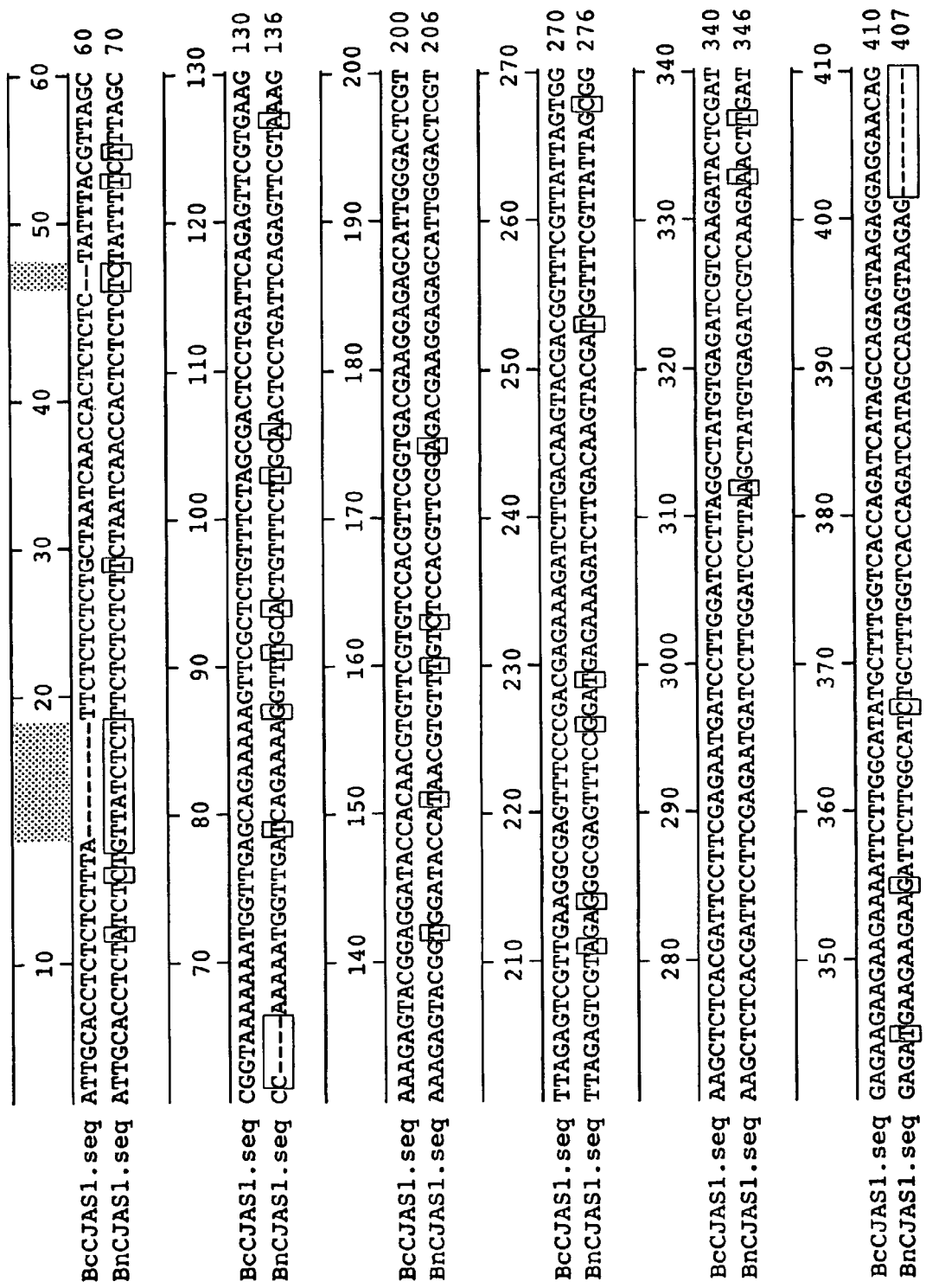

FIG. 6a: Sequence alignment of the 5'-ends of the original CJAS1 cDNA (SEQ ID NO: 1 from *Brassica carinata*), and the second homologous cDNA clone obtained from *Brassica carinata* (which is identical to the 5'-end of SEQ ID NO: 3, a full-length cDNA obtained from *Brassica napus*).

FIG. 6b: Sequence alignment of the amino-terminal ends of the predicted peptide sequence of the original CJAS1 gene product (SEQ ID NO: 2 from *Brassica carinata*), and the predicted peptide sequence shown in SEQ ID NO: 4.

FIG. 7: Manual alignment of selected regions from SEQ ID NO: 1 with the known peptide sequences from two domains of several class I glutamine amidotransferases (CJAS1 (SEQ ID NOS:13-15); TrpG (SEQ ID NOS:16-18); PabA (SEQ ID NOS:19-21); GuaA (SEQ ID NOS:22-24); CarA (SEQ ID NOS:25-27); PyrG (SEQ ID NOS:28-30); HisH (SEQ ID NOS:31-33); and PurL (SEQ ID NOS:34-36)).

FIG. 8: Sequence alignment of SEQ ID NO: 2 with homologous peptide sequences from *Arabidopsis thaliana* (SEQ ID NOS:38-42) identified from a BLAST search as described in Example 13. Also indicated is a majority sequence derived from the alignments (SEQ ID NO:37).

5. GLOSSARY OF TERMS

Amplification of DNA/amplified DNA: "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202, and in Innis et al. (eds.), PCR Protocols: A Guide to Methods and Applications, Academic Press, San Diego, 1990.

Construct: A construct comprises a vector and an insert operatively linked to the vector, such that the vector and insert can be replicated and transformed as required.

Expression: The generation of a protein product derived from a DNA sequence encoding the protein, comprising a combination of transcription and translation.

Expression cassette: A nucleotide sequence comprising a promoter in operable relationship with an open reading frame, or a complement thereof.

Homologous: DNA or peptide sequences exhibiting similarity to another DNA or peptide sequence in terms of the chemical nature, order and position of the individual residues relative to one another in the sequence. For the purposes of this application, unless stated otherwise, homology is characterized according to BLAST search results, wherein a best-fit sequence alignment is obtained. In this way, sequences comprising residues that are similar or identical may be aligned, and gaps provided as necessary. Homology is, therefore, expressed as a percentage of similarity or identity, wherein similarity encompasses both similar and identical residues. Unless stated otherwise, all BLAST searches were carried out using default parameters: e.g., gaps permitted, E-value=1, organism selected as required, filter for low complexity, standard genetic code, BLOSUM62 general purpose matrix; for more information see worldwideweb.ncbi.nlm.nih.gov/Education/BLASTinfo/tutl.html.

Identity: Comparison of homologous DNA or peptide sequences provides identification of residues that are identical in the same relative position of the sequence, following best-fit alignment. For the purposes of this application, unless stated otherwise, homology, best-fit alignment and identity are calculated according to BLAST search results (BLAST searching is available, for example, from the following website: worldwideweb.ncbi.nlm.nih.gov/BLAST/). Identity is provided as a percentage, indicating the percentage of residues that are identical along the sequences under comparison, excluding regions of gaps between the aligned sequences. BLAST searching permits a standard alignment configuration to automatically take into account regions of gaps or truncations between sequences, thereby providing a "best-fit" alignment.

Isolated: A nucleotide or peptide is "isolated" if it has been separated from other cellular components (nucleic acids, liquids, carbohydrates, and other nucleotides or peptides) that naturally accompany it. Such a nucleotide or peptide can also be referred to as "pure" or "homogeneous" or "substantially" pure or homogeneous. Thus, a nucleotide or peptide which is chemically synthesized or recombinant is considered to be isolate. A nucleotide or peptide is isolated when at least 60-90% by weight of a sample is composed of the nucleotide or peptide, preferably 95% or more, and more preferably more than 99%. Protein purity or homogeneity is indicated, for example, by polyacrylamide gel electrophoresis of a protein sample, followed by visualization of a single peptide band upon staining the polyacrylamide gel; high-performance liquid chromatography; or other conventional methods. The peptides of the present invention can be purified by any of the means known in the art. Various methods of protein purification are described, e.g., in Guide to Protein Purification, in Deutscher (ed.), Meth. Enzymol. 185, Academic Press, San Diego, 1990; and Scopes, Protein Purification: Principles and Practice, Springer Verlag, New York, 1982.

Lighter seed colour/lighter seed coat colour: a seed having a colour or having a seed coat colour that is lighter in colour than an average coloured seed from a non-transgenic unmodified plant. The term 'lighter' is used on the understanding that a natural variation will exist in the colour of seeds obtained from both a transgenic plant of the present invention, and a corresponding wild-type unmodified plant. Therefore, the term 'lighter' is used in consideration of an average seed colour or seed coat colour when comparing seeds obtained from transgenic and unmodified plants.

Organ: A specific region of a plant defined in terms of structure and function, for example in the case of a plant: a stem, a leaf, an anther, a pollen grain, or a root.

Promoter: A recognition site on a DNA sequence or group of DNA sequences that provides at least one expression control element for a gene encoding a polypeptide, and to which RNA polymerase specifically binds and initiates RNA synthesis (transcription) of the gene.

Reduced fibre content: relates to a seed derived from a transgenic plant of the present invention having a reduced fibre content when compared to a seed derived from a corresponding non-transgenic unmodified plant. The expression 'reduced fibre content' is used on the understanding that a natural variation will exist in the fibre content of seeds obtained from both a transgenic plant of the present invention, and a corresponding wild-type unmodified plant. Therefore, the expression 'reduced fibre content' is used in consideration of an average seed fibre content when comparing seeds obtained from transgenic and unmodified plants.

Stringent conditions: The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989, at 9.52-9.55. See also, Sambrook et al., 1989, at 9.47-9.52, 9.56-9.58; Kanehisa, Nucl. Acids Res. 12:203-213, 1984; and Wetmur and Davidson, J. Mol. Biol. 31:349-370, 1968. In general, wash conditions should include a wash temperature that is approximately 12-20° C. below the calculated $T_m$ (melting temperature) of the hybrid pair under study (Sambrook et al., 1989, pp. 9-51). Melting temperature for a hybrid pair may be calculated by the following equation:

$$T_m = 81.5° C. - 16.6(\log_{10}[Na^+]) + 0.41(\% G+C) - 0.63(\% \text{formamide}) - (600/L)$$

where L=the length of the hybrid in base pairs.

For example, typical conditions for hybridization under stringent conditions may be 65° C. 6×SSC.

Transformation: Modification of a cell by the introduction of exogeneous DNA sequence (e.g. a vector, construct or recombinant DNA molecule).

Transgenic: A cell or organism derived from a process of cellular transformation, wherein the cell or organism comprises the introduced exogenous DNA molecule not originally present in a non-transgenic cell or organism.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant.

Vector: A DNA molecule capable of replication in a host cell and/or to which another DNA segment can be operatively linked so as to bring about replication of the attached segment. A plasmid is an exemplary vector.

6. DETAILED DESCRIPTION OF THE INVENTION

The present invention describes nucleic acids commonly designated CJAS1, which encode proteins involved in seed metabolism in cruciferous plants. The inventors have determined that the homologous proteins encoded by CJAS1 are involved in the defense response found in plants and CJAS1 represents a new gene that shows only limited homology to genes previously described in the art. The CJAS1 sequence represents a gene also expressed during the formation of the typical dark seed coat in *Brassica*. The results demonstrate that the protein encoded for by CJAS1, when expressed normally in developing seeds, is involved in the formation of the normal dark seed coat found in many *Brassica* species, including seed coats that are high in fibre.

In this regard, the CJAS1 cDNA, when expressed in an antisense orientation in transformed plants that normally have dark seed coats with high crude fibre levels, unexpectedly leads to the formation of seed with yellow colored seed coats and/or with reduced crude fibre content.

Thus the present invention allows for the production of low fibre yellow seeds in *Brassica* varieties where dark seeded high fibre seeds are typically observed. It is fully anticipated that this discovery allows for the widespread development of low fibre or low fibre yellow seeded canola *Brassica napus* on a wide scale not previously possible using breeding or mutation techniques. Moreover, other plant species are considered amenable to corresponding modifications.

The isolation of the CJAS1 cDNA was initially accomplished from *Brassica carinata* as a result of the study of genes involved in phytoalexin biosynthesis. Phytoalexins are found in many tissues of the plant and are often associated with cellular defense and secondary metabolism. Phytoalexins are typically induced in response to pathogens such as fungi, and can also be induced by various chemical stresses. *Brassica* phytoalexins are formed as a result of plant encoded enzyme activities that utilize, in part, indole glucosinolates. The biosynthesis of indole glucosinolates has been an object of study for some time as glucosinolates are generally considered to be antinutritional in nature.

Regulation of phytoalexin biosynthesis is poorly understood, and identification of key regulatory steps has been an objective for plant scientists for some time. Phytoalexins are often found in seed coats as they are alleged to provide some protection against seed pathogens such as bacteria or fungi. Although individual phytoalexins are often not effective in controlling fungi, the complex mixture of phytoalexins, lignified tissues and other secondary metabolites in seed coats can provide a strong barrier to seed diseases. Accordingly, phytoalexin biosynthesis is likely to be regulated during the development of seed coats as well as at the level of pathogen invasion, thus showing regulation at many different levels.

Presently, little data exists regarding the genes involved in the phytoalexin biosynthesis. Therefore, the inventors examined the expression of genes induced upon induction of phytoalexin biosynthesis. Spraying plants with a solution of copper chloride (an elicitor of phytoalexin biosynthesisis) is known to induce the production of phytoalexins as well as other plant defense responses. Plant cells were treated with copper chloride and cDNA libraries were made that represented copper-chloride induced genes. As part of characterizing the multitude of genes that showed copper chloride induction, the cDNAs were sequenced and the sequences were compared to database entries (see Examples).

cDNAs that were specifically induced by copper chloride treatment and not present in the gene databanks were used in experiments with transgenic plants wherein said transgenic plants were made with a plant transformation vector that would express the antisense strand of the cDNAs in transformed plants. The application of this technique is well known in the art to reduce the expression of endogenous genes in the transformed plants and altered phenotypes can be observed.

Transformed plants containing these antisense gene vectors were visually examined for altered phenotypes. As a result of this analysis, surprisingly one of the transformation vectors, comprising an antisense gene utilizing the CJAS1 cDNA (SEQ ID NO: 1) caused altered seed coat color. The inventors observed that over 50% of the transformants for the CJAS1 cDNA antisense produced a lighter coloured (yellow) seed, which contrasted to the darker seeds of the unmodified plants. These yellow seeds gave rise to plants that segregate in a 3:1 ratio for production of yellow seed. In addition to alteration of seed coat color, the transgenic plant seeds also showed a significant reduction in crude fibre content (see examples).

Therefore, the present invention encompasses the discovery that the inhibition of the plant gene corresponding to the CJAS1 cDNA (by antisense expression) can lead to the production of reduced fibre yellow seeds in *Brassica* varieties where dark seed coats are usually found (see examples). The genetics of segregation of the trait suggest that a single insertion event is sufficient to confer the yellow seed phenotype. Reduced fibre content was also observed (see examples). Decreasing the expression of this gene appears to have the ability to alter both seed coat color and fibre content of seed. Accordingly, a novel method for the production of low fibre and/or yellow seeded canola from varieties of dark seeded canola has been discovered.

The present invention encompasses the CJAS1 cDNA sequence isolated from *Brassica carinata* (SEQ ID NO: 1) as well as other homologous nucleotide sequences derived from *Brassica carinata* and other species of plant, and the use of such homologous nucleotide sequences for the production of transgenic plants comprising seeds with lighter colour and reduced fibre content. Such homologous sequences can be obtained by any one of the following techniques:

1) DNA Library Screening

The nucleotide sequences of the present invention can be used to produce (degenerate) nucleotide probes, for the purposes of screening cDNA and genomic DNA libraries of various plant species. Related techniques are well understood in the art, for example as provided in Sambrook et al., *Molecular Cloning: A Laboratory Manual*, Cold Spring Harbor Press, Cold Spring Harbor, N.Y.(1989). In this way, sequences homologous to those of the present application are readily obtainable. For this reason, it is the intention of the present invention to encompass polynucleotide molecules comprising DNA sequences that encode peptides with significant sequence identity to those disclosed in the present application, wherein SEQ ID NOS: 1, 3, or 5, or parts thereof, are utilized as polynucleotide probes to search for and isolate homologous polynucleotide molecules. Moreover, polynucleotides encoding proteins with significant sequence identity to those of the present application are expected to give rise to similar protein products with similar biochemical characteristics, to those described in the present invention.

By using DNA library screening and PCR amplification techniques the inventors have succeeded in obtaining a full-length CJAS1 homologous cDNA from *Brassica napus* (SEQ ID NO: 3), a partial CJAS1 homologous cDNA from *Brassica carinata* (which was identical to the 5'-end of SEQ ID NO: 3), as well as a partial cDNA of another homologous gene from *Brassica napus* (SEQ ID NO: 5-see later). More details in this regard are provided in the examples.

2) Computer-based Homology Searches

The nucleotide and amino acid sequences disclosed in the present application can be used to identify homologous nucleotide and peptide sequences via computer-based searching techniques (for example, BLAST searches are available through the website at worldwideweb.ncbi.nlm.nih.gov/BLAST/). Such techniques are very familiar to persons of skill in the art, and can be readily utilized to identify homologous nucleotide and peptide sequences that may be used in accordance with the teachings of the present application.

BLAST searches have been successfully used by the inventors to identify CJAS1 homologues in *Arabidopsis thaliana*, which may be cloned and used to generate transgenic plants comprising seeds with reduced fibre content or lighter colour, in accordance with the present invention. More details in this regard are provided in the Examples.

The present invention therefore encompasses DNA sequences obtained by techniques known in the art for isolating homologous DNA sequences, wherein the techniques utilize degenerate oligonucleotide probes derived from a sequence selected from SEQ ID NO:1, 3, and 5, or parts thereof. Alternatively, the techniques may utilize known sequence alignment programs that search databases such as Genbank for homologous nucleotide and peptide sequences.

The degree of amino acid sequence homology will vary for each identified sequence. It is the intention of the present invention to encompass polynucleotide sequences comprising at least 50% sequence homology with regard to the peptide sequences encoded by the corresponding polynucleotides. Without wishing to be bound by theory, it is generally expected in the art that enzymes with at least 50% homology can be expected to have enzymatic activities that are similar in scope. In this regard, the essential structural features of the enzyme are preserved to scaffold the conformation of the catalytic site of the enzyme. Therefore, the present invention encompasses polynucleotide molecules derived by screening genomic and cDNA libraries of species other than *Brassica carinata* and *Brassica napus*, using degenerate DNA probes derived from the sequences of the present application. Such species include, but are not restricted to: other cruciferous species and species included in the genus *Brassica*.

The present invention also encompasses polynucleotide sequences obtained by screening DNA libraries using degenerate oligonucleotide probes derived from the polynucleotides of the present invention, or from sequence alignments derived from suitable nucleotide databases (e.g. Genbank), wherein the sequences encode peptides comprising at least 70% amino acid sequence homology to peptides encoded by SEQ ID NOS: 1, 3, and 5. In this regard, homologous proteins with at least 70% predicted amino acid sequence homology are expected to encompass proteins with activity as those defined by the present invention, wherein disruption of expression of the homologous proteins is expected to generate plants comprising seeds with reduced fibre content and/or a lighter colour. Such proteins may be derived from similar species of plant.

The present invention also encompasses polynucleotide sequences encoding peptides comprising at least 90% or 95% sequence homology to the peptides encoded by SEQ ID NOS: 1, 3, and 5. This class of related proteins is intended to include close gene family members with very similar or identical catalytic activity. In addition, peptides with 90% to 95% amino acid sequence homology may be derived from functional homologues of similar species of plant, or from directed mutations to the sequences disclosed in the present application.

It will also be understood to a person of skill in the art that site-directed mutagenesis techniques are readily applicable to the polynucleotide sequences of the present invention. Related techniques are well understood in the art, for example as provided in Sambrook et al., *Molecular Cloning: A Laboratory Manual*, Cold Spring Harbor Press, Cold Spring Harbor, N.Y.(1989). In this regard, the present invention teaches the isolation and characterization of the DNA sequences as provided as SEQ ID NOS: 1, 3, and 5. However, the present invention is not intended to be limited to these specific sequences. Numerous directed mutagenesis techniques would permit the non-informed technician to alter one or more residues in the nucleotide sequences, thus changing the subsequently expressed polypeptide sequences. Moreover, commercial 'kits' are available from numerous companies that permit directed mutagenesis to be carried out (available for example from Promega and Biorad). These include the use of plasmids with altered antibiotic resistance, uracil incorporation and PCR techniques to generate the desired mutation. The mutations generated may include point mutations, deletions and truncations as required. The present invention is therefore intended to encompass corresponding mutants of the CJAS1 cDNA and genomic DNA sequences disclosed in the present application.

The polynucleotide sequences of the present invention must be ligated into suitable vectors before transfer of the genetic material into plants. For this purpose, standard ligation techniques that are well known in the art may be used. Such techniques are readily obtainable from any standard textbook relating to protocols in molecular biology, and suitable ligase enzymes are commercially available.

The present invention also encompasses isolated and purified peptides encoded by the nucleotides sequences of the present invention. The present invention also encompasses polyclonal and/or monoclonal antibodies that are specific for the peptides of the present invention and are capable of distinguishing the peptides of the present invention from other polypeptides under standard conditions. Such antibodies can be generated by conventional methods. For the preparation and use of antibodies according to the present invention, including various immunoassay techniques and applications, see, e.g., Goding, Monoclonal Antibodies: Principles and Practice, 2d ed., Academic Press, New York, 1986; and Harlow and Lane, Antibodies: A Laboratory Manual, Cold Spring Harbor Laboratory, Cold Spring Harbor, N.Y. 1988. The peptides and antibodies of the present invention can be labeled by conventional techniques. Suitable labels include radionuclides, enzymes, substrates, cofactors, inhibitors, fluorescent agents, chemiluminescent agents, magnetic particles, etc.

The present invention also encompasses a plant cell transformed with a nucleotide sequence of the present invention, and as well as plants derived from propagation of the transformed plant cells. Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The following are examples, and are not limiting:

A. *Agrobacterium*-mediated Transformation: One method for introducing an expression vector into plants is based on the natural transformation system of *Agrobacterium*. See, for example, Horsch et al., Science 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci. 10: 1 (1991). Descriptions of *Agrobacterium* vector systems and methods for *Agrobacterium*-mediated gene transfer are provided by Gruber et al., supra, Miki et al., supra, and Moloney et al., Plant Cell Reports 8: 238 (1989). Bechtold et al., C. R. Acad. Sci. Paris Life Sciences, 316:1194-9 (1993).

B. Direct Gene Transfer: Several methods of plant transformation, collectively referred to as direct gene transfer, have been developed as an alternative to Agrobacterium-mediated transformation. A generally applicable method of plant transformation is microprojectile-mediated transformation wherein DNA is carried on the surface of microprojectiles measuring 1 to 4 .mu.m. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5: 27 (1987), Sanford, J. C., Trends Biotech. 6: 299 (1988), Klein et al., Bio/Technology 6: 559-563 (1988), Sanford, J. C., Physiol Plant 79: 206 (1990), Klein et al., Biotechnology 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc Natl. Acad. Sci. U.S.A. 84: 3962 (1987). Direct uptake of DNA into protoplasts using $CaCl_2$ precipitation, polyvinyl alcohol or poly-L-ornithine have also been reported. Hain et al., Mol. Gen. Genet.199: 161 (1985) and Draper et al., Plant Cell Physiol.23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Following transformation of target cell(s) or tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety.

Alternatively, a genetic trait which has been engineered into a particular line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context. Once a transgenic plant has been established, it is important to determine the phenotype of the seeds of the plant. Accordingly, in a preferred embodiment of the invention a method is provided for modifying the seed of a plant comprising the steps of:

(a) introducing into a plant cell capable of being transformed and regenerated into a whole plant a construct comprising, in addition to the DNA sequences required for transformation and selection in plants, a nucleotide sequence in accordance with the nucleotide sequences encompassed by the present invention, operably linked to a promoter; and (b) recovery of a plant which contains nucleotide sequence.

It is apparent to the skilled artisan that the polynucleotide CJAS1 can be in the antisense (for inhibition by antisense RNA) or sense (for inhibition by co-suppression) orientation, relative to the transcriptional regulatory region, or a combination of sense and antisense RNA to induce double stranded RNA interference (Chuang and Meyerowitz, PNAS 97: 4985-4990, 2000, Smith et al., Nature 407: 319-320, 2000). Other methods of gene inhibition can also be contemplated within the scope of the present invention.

A transcriptional regulatory region is often referred to as a promoter region and there are numerous promoters that can be used within the scope of the present invention. A preferred promoter would be a promoter that limits the expression of the antisense gene to seed tissue or tissue within the seed that contributes or is involved in the formation of seed coat. Suitable promoters would include the *Brassica napin* and cruciferin promoters, the bean phaseolin promoter or the soybean conglycinin promoter. Alternative promoter types may include, but are not limited to: constitutive promoters, induceable promoters, organ-specific promoters, developmental-specific promoters, strong promoters, weak promoters etc.

Importantly, the present invention encompasses transgenic plants, and the products and seeds thereof, which are generated by the methods of the present invention, wherein the nucleotide sequences of the present invention are transformed and expressed in the plant species of choice. The transgenic plants of the present invention are not limited with regard to plant species, provided that the transformation and expression of the nucleotide sequence of the present invention in the plant gives rise to the desired phenotype regarding seeds with reduced fibre content and/or lighter colour. Particularly preferred species include cruciferous varieties, and varieties of the genus *Brassica*. Most preferred plant species include *Brassica carinata* and *Brassica napus*, from which the CJAS1 homologous nucleotide sequences have thus far been identified.

It is also possible to use more recently developed strategies for the manipulation of the expression of CJAS1 related sequences. The use of ribozymes is within the skill ordinarily found in the art as a mechanism of reducing the expression of CJAS1 related genes. Genomic DNA library screening and chromosome walking are further techniques that are well known to those of skill in the art as described for example in Sambrook et al., Molecular Cloning: A Laboratory Manual, Cold Spring Harbour N.Y. (1989). Such techniques can be readily used to obtain promoter sequence for the CJAS1 genes and to isolate the genomic DNA encoding the CJAS1 polypeptide. In this way the expression of CJAS1 under normal conditions of seed development can be evaluated. The promoter region can be isolated and studied in order to further devise methods for controlling gene expression of this and related gene families.

In terms of the function of the CJAS1 encoded protein, the derived amino acid sequence of CJAS1 had 63% identity to a GMP synthase like protein of *A. thaliana* (accession AAC63665 & AAC63681). The ORF of CJAS1 encoded a polypeptide of 250 amino acids with a calculated molecular mass of 28.4 kDa. The polypeptide contained two domains with several amino acids each typifying class I glutamine amidotransferases (GMP synthase) (KILGICFGHQ and HL FCIQGHPEYN) (SEQ ID NOS:11 and 12).

The cDNA was inserted into an expression vector and transformed into the *Escherichia.coli* GMP synthetase mutant ght1 (Van Lookeren Campagne et al., J. Biol. Chem. 266, 16448-16452 1991) but no complementation was observed. Thus, it is postulated that the protein encodes an amidotransferase activity distinct from GMP synthase that utilizes an aromatic compound for a substrate. This is analogous to a similar step seen for the phenylpropanoid pathway, another pathway that is involved in the formation of fibre (and the seed coat) and is a pathway that utilizes aromatic compounds. In the phenylpropanoid pathway, L-phenylalanine, an aromatic amino acid, is a substrate for the enzyme phenyalanine ammonia lyase (PAL). The enzymatic activity of PAL leads to the formation of cinnamic acid by deamination which eventually leads to the formation of lignin monomers. In the present case, CJAS1 may be a subunit of an enzyme that encodes a lyase activity utilized within another secondary metabolite pathway and reduction of the enzyme activity (as evidenced by antisense RNA inhibition of the gene expression) can lead to alteration in the formation of phenolic-related compounds. This alteration may further affect the formation of other compounds in the seed, in particular compounds that are known to be related to fibre formation.

The following Examples serve to illustrate the present invention but should not be regarded as limiting the scope of the invention in any way.

EXAMPLE 1

Cloning of Genes Induced by Copper Chloride Treatment

In this example, differential screening of induced and non-induced plant cells was used to isolate cDNAs preferentially induced by copper chloride treatment. *Brassica carinata* (breeding line C90-1163, Agriculture and Agri-Food Canada Research Station, Saskatoon) were grown in Terra-Lite-Redi-Earth amended with Nutricote 14-14-14 fertilizer. The plants were grown in a Conviron Model PGV36 growth chamber at 21/19° C. day/night temperatures with a 16 h photoperiod. Light intensity was 180/µEs/m$^2$, provided by Sylvania extended service 40 W incandescent bulbs and Sylvania cool white fluorescent 215 W bulbs. Plants of the species *Brassica carinata* were treated with 5 mM copper chloride by spraying leaves until runoff. Total RNA was extracted from the leaves of 4 week old *Brassica carinata* plants 12 hours after spraying with $H_2O$ or 5 mM $CuCl_2$. Poly(A)$^+$ RNA was isolated from the total RNA using oligo(dT)-cellulose resin (Life Technologies) according to published procedures (Wu, W. (1997) Methods in Gene Biotechnology. Boca Raton, Fla.: CRC Press). The XhoI and PacI oligo-dT primer was used to prime the synthesis of the single-stranded cDNA from the RNA of $CuCl_2$-treated leaves. Second strand synthesis and cloning were carried out according to the manufacturer's instructions in the λZAP II cDNA synthesis kit (Stratagene).

In vivo mass extinction was performed on the λZAP II cDNA following the manufacturer's instructions (Stratagene). The phagemid DNA was isolated from 192 randomly selected colonies and approximately 100 ng of each DNA sample was dot-blotted onto duplicate Hybond-N nylon membranes (Amersham Pharmacia Biotech). RNA from $H_2O$ and $CuCl_2$ treated leaves was reverse-transcribed (Superscript II) into sscDNA primed by oligo-dT following the supplier's instructions (Life Technologies). The resulting DNA was labelled using High Prime (Roche Molecular Biochemicals). The hybridization was conducted overnight at 42° C. in 50% (v/v) formamide, 5× SSPE (20× SSPE, pH 7.4=174 g/l NaCl, 27.6 g/l $NaH_2PO_4,H_2O$, 7.4 g/l $Na_2EDTA$) 5× Denhardt (50× Denhardt=10 g/l ficoll approx. mol. weight 400 kDa, 10 g/l polyvinylpyrrolidone m.w. 360 kDa, 10 g/l bovine serum albumen) 0.5% (w/v) SDS and 100 µg/ml of single stranded fish DNA (Roche Molecular Biochemicals). The membranes were washed in 2×SSC (1×SSC, pH7.0=: 0.15 M NaCl, 0.015 M sodium citrate), 0.5% (W/V) SDS at room temperature for 15 min followed by three washes in 0.2×SSC, 0.2% (w/v) SDS at 60-65° C. for 15 min each, then exposed to X-ray film (Kodak, XAR-5) for autoradiography. Rapid amplification of 5'-cDNA ends was performed using the 5'-RACE System (Version 2.0) kit as described in the manufacturer's instructions (Life Technologies). The PCR products were cloned into the vector pCR2.1 (Invitrogen) for sequencing.

A number of the sequences showed similarity to known genes, particularly genes involved in the defense response. These sequences were not studied further. However, a small number of the cDNAs were not homologous to known sequences and these cDNAs were specifically identified as unique defense-related sequences. The sequence of one of these cDNAs, CJAS1, is shown as SEQ ID NO:1. The derived amino acid sequence of CJAS1 is shown as SEQ ID NO:2.

EXAMPLE 2

Construction of Antisense Genes Using Defense-Related Sequences cDNAs that were specifically induced by copper chloride and not homologous to any genes with known functions were used to construct antisense RNA transformation vectors. Plant transformation vectors comprising a duplicated 35S promoter for the expression antisense sequences were used. The transformation vector was RD400 (Datla, R. S. S., Hammerlindl, J. K., Panchuk, B., Pelcher, L. E., and Keller, W., 1992, Gene 211:383-384).

The plant transformation vectors used for the construction of antisense RNA genes were constructed by inserting (ligating) the defense-related cDNAs in the antisense orientation relative to the double 35S promoter using standard vector/insert ligation techniques. The orientation of the cDNAs was confirmed by restriction mapping. The restriction map of the cDNA inserted into the vector is shown in FIG. 1.

EXAMPLE 3

Transformation of Plants with Antisense Transformation Vectors

The plant transformation vectors carrying the antisense genes made with the defense-related cDNAs were used for plant transformation. The plant species used for transformation was a selection of *Brassica carinata*, the same selection that was originally treated with Copper chloride. This selection of *B. carinata* has dark colored, thick seed coats. For transformation, *Agrobacterium tumifaciens* strain GV3101/pMP90 (Koncz C. & Schell, J., 1986, Mol. Gen. Genet. 204: 383-396) was used. The transformation vectors were introduced into the *Agrobacterium* strain using standard techniques. Plant explants were co-cultured for 3 days then transferred to selective media. Plants were selected on kanamycin.

EXAMPLE 4

Isolation of Yellow Seeded Transformed Plants

Transformed *B. carinata* were analyzed by visual characterization. Of five independent cDNAs analyzed by the method of antisense RNA expression in planta, one vector composed of the CJAS1 cDNA (SEQ ID NO: 1) in the antisense orientation produced numerous transformed plants that had yellow colored seed coats. The control transgenic plants, as well as the plants transformed with the four other cDNAs had predominantly dark colored seed coats. A sample comparison of seeds obtain from wild-type *Brassica carinata* and transgenic *Brassica carinata* expressing antisense CJAS1 (SEQ ID NO: 1) is shown in FIG. 2a and FIG. 2b.

EXAMPLE 5

Segregation of the Yellow Seed Trait

Transformed plants composed of the CJAS1 cDNA in the antisense orientation under the control of the 35S promoter were selfed and the resultant progeny grown out and observed for the presence of yellow seeds. It was found that in most plant lines a 3:1 ratio of yellow to dark colored seeds were observed, indicating a single locus of insertion for the antisense gene.

EXAMPLE 6

Fibre Content of Transformed Lines

Seed from transgenic and non-transgenic lines was analyzed for crude fibre content. Percent crude fiber, acid detergent fiber and neutral detergent fiber methods were carried out as described in the book Dietary fiber Analysis and Applications (sections or methods designations), 7.061-7.065 published by the Association of Official Agricultural Chemists, and National Forage Testing Association procedures 4.1, and 5.1. Each independently derived transgenic line is assigned a designation as an event. These events are referred to as *B. carinata* Events in Table 1. Out of 13 transgenic lines analyzed, 5 showed a greater than 30% reduction in crude fibre content, while 4 more lines showed a statistically reduced level of crude fibre. Thus nine out of thirteen transgenic lines showed a reduction in fibre content as a result of the expression of the CJAS1 cDNA (SEQ ID NO: 1) in an antisense orientation.

The percent crude fibre (representing the lignin, cellulosic, hemicellulosic and pectin fractions) of all the transgenic events tested were lower than the null control (Table 1 and FIG. 3). The largest reduction in crude fibre content was observed from event 90-18-1, which was 36.3% lower than the null control (Table 1 and FIG. 3). Four other independent events 90-6-1, 90-17-1, 90-25-1 and 90-34 were found to have crude fibre levels at least 30% lower than the null control (FIG. 3).

Table 1. Summary of the fibre analysis from greenhouse grown transgenic *Brassica carinata*. Values are expressed as the mean of two independent determinations. Percent crude fibre, acid detergent fibre and neutral detergent fibre methods were carried out as described in AOAC 7.061-7.065, NFTA 4.1, NFTA 5.1, (Designations for methods outlined by the Association of Official Agricultural Chemists and the National Forage Testing Association, see above).

| B. Carinata Event | % Crude Fibre (D.B.) | % ADF (D.B.) | % NDF (D.B.) |
| --- | --- | --- | --- |
| Null Control | 6.2 | 8.7 | 11.7 |
| Non-Transformed Control | 5.1 | 7.8 | 11.8 |
| 90-18-1 | 3.9 | 5.2 | 11.9 |
| 90-20 | 4.6 | 7.9 | 12.6 |
| 90-4 | 5.1 | 8.5 | 10.3 |
| 90-19 | 4.8 | 7.1 | 11.1 |
| 90-7-1 | 5.5 | 8.0 | 10.6 |
| 90-15 | 4.7 | 8.2 | 11.1 |
| 90-11 | 4.7 | 7.1 | 10.5 |
| 90-6-1 | 4.3 | 6.4 | 10.1 |
| 90-17-1 | 4.1 | 5.9 | 11.6 |
| 90-25-1 | 4.1 | 6.4 | 10.1 |
| 90-29-1 | 4.9 | 7.4 | 11.5 |
| 90-34-1 | 4.2 | 5.8 | 10.2 |
| 90-30-1 | 4.6 | 6.9 | 12.0 |

The acid detergent fibre content of all transgenic events tested was reduced when compared to the null control (FIG. 4). The acid detergent fibre (ADF) analysis tends to measure the cellulosic and acid stable lignin residues that are not acid soluble. Event 90-18-1 was observed to have a 40% reduction in ADF content when compared to the null control (Table 1 and FIG. 4). The five events (90-18-1, 90-6-1, 90-17-1, 90-25-1 and 90-34) with the largest reduction in crude fibre (FIG. 3) were also found to have the greatest reduction in ADF content when compared to the null control (FIG. 4). The data suggests that the acid insoluble lignin and cellulosic fractions of these five events are reduced when compared to the null control.

The neutral detergent fibre (NDF) analysis tends to measure the lignin (insoluble and acid soluble), cellulosic, and hemicellulosic fractions present in the meal. Events 90-6-1, 90-25-1 and 90-34-1 had reductions in NDF of 13.5%, 13.9%, and 13.3%, respectively (FIG. 5). Events 90-6-1, 90-25-1 and 90-34-1 also had some of the largest reductions in crude fibre and ADF (FIG. 3 and FIG. 4).

EXAMPLE 7

Transformation of *Brassica napus* Plants with Antisense Transformation Vectors

In this example, the plant transformation vector composed of the CJAS1 cDNA (SEQ ID NO: 1) in the antisense orientation was used for plant transformation of *Brassica napus* that has dark colored, thick seed coats. For transformation, *Agrobacterium tumifaciens* strain GV3101/pMP90 (Koncz C. & Schell, J., 1986, Mol. Gen. Genet. 204:383-396) was used. The transformation vector was introduced into the *Agrobacterium* strain using standard techniques. Plant explants were co-cultured for 3 days then transferred to selective media. Plants were selected on kanamycin. Numerous transgenic plants lines were recovered and selfed and seed coat color analyzed. The results are shown in Table 2 below, and illustrate that the expression of CJAS1 (SEQ ID NO: 1) in an antisense orientation is also capable of generating lighter seed coat colour in plant species other than *Brassica carinata*.

Table 2: Summary of the seed coat colour analysis from greenhouse grown transgenic *Brassica napus* for different transformation events. The same transformation construct was used as described in previous examples. Seeds were individually rated by visual inspection. The average seed colour of the majority of the tranformation event was lighter than for the wild-type unmodified *Brassica napus*.

EXAMPLE 8

CJAS1 Expression in *B. carinata*

CJAS1 gene expression was studied via Northern blot of various plant tissues taken from wild-type *Brassica* plants (data not shown).

The CJAS1 gene was found to have a low constitutive expression in many tissues—root, stem, leaf, flower bud and silique. The amount of transcript in flower bud and silique was slightly greater than in the other tissues. The amount of transcript was further increased by Cu, MeJA, SA and ABA treatment. Interestingly, the timing of increased transcript accumulation for CJAS1 differs among treatments. The rapid response to Cu and MeJA implies a control mechanism sensitive to membrane damage. The activation of CJAS1 transcription by the four different compounds is unusual but not without precedent.

EXAMPLE 9

Inhibitors Effects on Expression of BcCJAS1

The effects of the nitric oxide (NO) scavenger 2-phenyl-4, 4,5,5-tetramethylimidazolinone-3-oxide-1-oxyl (PTIO), the protein phosphatase type 1 and 2A inhibitor okadaic acid (OKA), the serine/threonine protein kinases inhibitor staurosporine (STAU) and the protein translation inhibitor cycloheximide (CHX) were determined on induction/expression of CJAS1 in *Brassica carinata*. The data from these inhibitor studies (not shown) suggest that expression of CJAS1 is actively suppressed or the transcript is rapidly turned over by a labile protein or proteins that require phosphorylation. The STAU acted synergistically with MeJA in induction of CJAS1 expression. Also in the non-induced material PTIO, OKA, STAU and cycloheximide all increased CJAS1 transcript accumulation. It is difficult to understand how NO scavenging would de-repress transcription but inhibition of L-type $Ca^{2+}$ channels in rabbit glomus cells by NO was recently reported. Therefore, PTIO treatment may have indirectly led to an increase in $Ca^{2+}$ channel activity which in turn may have stimulated CJAS1 transcription.

| Event | Insertion # | Color 1-5 1 = Black, 5 = Yellow | Event | Insertion # | Color 1-5 1 = Black, 5 = Yellow |
|---|---|---|---|---|---|
| YSXX1 | | 2 | 1.0–2.0 | YSXX22 | 6 | 0.5–2.0 |
| YSXX2 | | 5 | 1.5–2.5 | YSXX23* | 1 | 0 | 0.5–2.5 |
| YSXX3 | | 2 | 0.5–1.5 | YSXX25 | 3 | 0.5–1.5 |
| YSXX4 | | 5 | 0.5–3.0 | YSXX26 | 1 | 0.5–1.5 |
| YSXXS* | 3,6 | 3 | 0.5–2.5 | YSXX27 | 3 | 0.5–2.0 |
| YSXXB | | 2 | 0.5–2.0 | YSXX29 | 2 | 0.5–1.5 |
| YSXX9 | | 6 | 1.0–2.0 | YSXX30* | 4,6 | 3 | 0.5–3.0 |
| YSXX10 | | 3 | 0.5–2.0 | YSXX32* | 3 | 4 | 0.5–2.5 |
| YSXX11 | | 2 | 0.5–2.5 | YSXX34 | | 1.0–2.0 |
| YSXX12 | | 2 | 0.5–1.5 | YSXX36 | | 0.0–1.5 |
| YSXX13 | | 2 | 2.0 | YSXX37 | | 0.0–0.5 |
| YSXX14* | 1 | 0 | 0.5–1.5 | YSXX38 | | 0.0–1.5 |
| YSXX15 | | 2 | 1.0–1.5 | YSXX39 | | 0.5–2.0 |
| YSXX17 | | 4 | 0.5–1.0 | YSXX40 | | 0.5–1.0 |
| YSXX18 | | 5 | 0.5–1.5 | YSXX43 | | 0.0–1.0 |
| YSXX20 | | 2 | 0.5–2.0 | YSXX45 | 7 | 0.5–1.5 |
| YSXX21* | 1 | 3 | 1.0–3.0 | YSXX46 | | 0.5–1.5 |

These results suggest that the CJAS1 gene may be involved in normal housekeeping functions as well as stress response.

Southern blot analysis indicated that the gene is present in 2-4 copies in the *B. carinata* genome.

EXAMPLE 10

Isolation of a Second CJAS1 Homologous cDNA from *Brassica carinata*

The inventors of the present application used the Invitrogen Generacer 5' RACE kit (according to the manufacturer's instructions) and RNA isolated from *B. carinata* leaf tissue sprayed with 5 mM $CuCl_2$, to determine whether additional nucleotide sequences can be isolated that are homologous to *Brassica carinata* CJAS1 (SEQ ID NO: 1). The corresponding protocol ensures the amplification of only full-length mRNA by eliminating truncated transcripts prior to the amplification process. The method is mRNA cap-dependent, thereby selecting for only those mRNAs that are full-length and contain both a 5' cap structure and a 3' polyA tail. A cDNA of interest was subsequently amplified using gene specific primers based on the initial 1044 base pair CJAS1 cDNA sequence (SEQ ID NO: 1). The primers used for the PCR amplification are shown below:

```
                                    (SEQ ID NO: 6)
TW1 = 5'CCTTCACGATGGTTATGTCTGTAAG3'

(SEQ ID NO: 7)
TW2 = 5'CTCTTACTCTGGCTATGATCTGGTGACC3'
```

This procedure resulted in the amplification and purification of a 409 base pair cDNA fragment from *Brassica carinata* that was homologous to SEQ ID NO:
1. A sequence alignment of the 5' end of the Generacer-derived *B. carinata* product indicates that this cDNA (which corresponds to the 5'-end of SEQ ID NO:
3) and the originally identified CJAS1 cDNA (SEQ ID NO: 1) are not identical. In this regard, the nucleotide and peptide sequence alignments, as shown in FIGS. 6a and 6b respectively, illustrate an 86% similarity over this region with 49 nucleotides (and 5 amino acids) differing between the two sequences in the first 409 bp. The majority of the nucleotide differences were found in the 5'-untranslated region including an insertion of ten nucleotides in the Generacer product not found in the original CJAS1 cDNA clone. However, four additional nucleotides were present in the original CJAS1 cDNA not found in the Generacer product. Three of the amino acid changes were conservative but the remaining two were substitutions of basic amino acids for non-polar amino acids.

Therefore a slight sequence variation was present in the two copies of the CJAS1 gene in *Brassica carinata*, with concomitant amino acid variation. The CJAS1 gene encodes a putative glutamine amidotransferase domain. Based on similarity to database proteins, it is likely to be a subunit of a heterodimeric enzyme.

EXAMPLE 11

Isolation of Homologs of BcCJAS1 from *Brassica napus*

Using total RNA isolated from *Brassica napus* leaves sprayed with 5 mM $CuCl_2$, the inventors performed the Generacer 5' RACE protocol in accordance with Example 10, using the same primers (SEQ ID NOS: 6 and 7). In this way, the inventors succeeded in isolating a partial cDNA *Brassica napus* nucleotide sequence which was identical to the partial CJAS1 sequence obtained from *Brassica carinata* in Example 10. Using the sequence of this *Brassica napus* product, a gene specific primer was designed to amplify the full-length *Brassica napus* cDNA. The primers used for the amplification of the full-length *Brassica napus* product were oligo-dT and the primer shown below:

```
TW8=5'ATTGCACCTCTATCTCTGTTATCTCTT3'
    (SEQ ID NO: 8)
```

In this way, PCR amplification successfully enabled the isolation of the full-length CJAS1 homologue from *Brassica napus*, and the sequence of the cDNA was characterised using standard DNA sequencing techniques. The sequence of the full-length cDNA product is shown in SEQ ID NO: 3, and the corresponding predicted peptide sequence is shown in SEQ ID NO: 4.

In addition to the full-length *Brassica napus* CJAS1 cDNA (SEQ ID NO: 3), a partial cDNA sequence was also obtained for a CJAS1-like gene using the following primers based on *Arabidopsis thaliana* genes sequence:

```
                                    (SEQ ID NO: 9)
TW10 = 5'CAAAAGAAGTACCTATTGTTT3'
based on gbAAC63681

(SEQ ID NO: 10)
TW12 = 5'AAAGCATCATGTGGACTA3'
based on embCAB79773
```

The sequence of this additional CJAS1-like partial cDNA obtained from *Brassica napus* is shown in SEQ ID NO: 5.

EXAMPLE 12

Southern Blot Analysis of *B. napus*

Southern blot analysis was performed (in accordance with Sambrook et al., *Molecular Cloning: A Laboratory Manual*, Cold Spring Harbor Press, Cold Spring Harbor, N.Y.(1989)) on *Brassica napus* to estimate gene copy number, examine gene variation and determine if related genes were present. The DNA was digested with BamHI, EcoRI, and SalI. BamHI is the only one of the three enzymes that cuts within the cDNA sequence and, therefore, should yield two hybridizing fragments. Each digest was run on a gel and the blot was probed with a short 5' *B. napus* Generacer product, comprising the first 409 nucleotides of SEQ ID NO: 3. Low stringency washes were done and the blot was developed by autoradiography.

As expected, two strongly hybridizing fragments were observed in the BamHI genomic digest lane that correspond to near identical copies of the CJAS1 gene. Four faintly hybridizing fragments were also observed in this digest. One strongly hybridizing fragment was present in EcoRI digested DNA. An additional one to two faintly hybridizing fragments were observed in this digest. Only a single strongly hybridizing fragment was observed in the SalI digested DNA. Therefore, CJAS1 is not a member of a closely related gene family. There could be two to four distantly related genes in the *B. napus* genome.

EXAMPLE 13

Identification of Nucleotide and Peptide Sequences with Homology to the CJAS1 Gene (and Encoded Peptide) via Computer-based Sequence Database Searching The inventors have manually generated an alignment of the derived amino acid sequence of CJAS1 (taken from SEQ ID NO: 1) with the G-type GAT domains of several bacterial amidotransferase, as shown in FIG. 7. Although sequence similarity clearly exists, it is apparent that the CJAS1 cDNA does not encode a synthase domain (not shown in FIG. 7).

The nucleotide and derived amino acid sequence of the CJAS1 cDNA (SEQ ID NO: 1) was also used in a BLAST search of the nucleotide and protein databases at NCBI using default parameters. The results revealed an *Arabidopsis thaliana* genomic sequence from BAC F17I23 (accession AF160182) that had 86% identity to the CJAS1 cDNA. Three other related proteins comprised 59-70% homology to SEQ ID NO: 1. This similarity in the cruciferous family of plants is not unexpected. It is anticipated that homologous activities in other plant species can be found. The peptide sequence alignments for the predicted peptide sequence encoded by SEQ ID NO:1 (i.e. SEQ ID NO: 2) together with the five corresponding *Arabidopsis thaliana* peptide sequences identified by the BLAST searching, are illustrated in FIG. 8.

SEQUENCE LISTING FREE TEXT

SEQ ID NO: 6 TM1 primer
SEQ ID NO: 7 TM2 primer
SEQ ID NO: 8 TM8 primer
SEQ ID NO: 9 TM10 primer
SEQ ID NO: 10 TM12 primer

The invention claimed is:

1. An isolated nucleotide sequence comprising the nucleotide sequence of SEQ ID NO: 1 encoding the polypeptide of SEQ ID NO: 2.

2. An isolated nucleotide sequence comprising an antisense sequence of SEQ ID NO: 1 operably linked to a promoter, wherein the expression of the nucleotide sequence in a plant reduces the fiber content of seeds of the plant compared to seeds of a wild-type or non-transgenic plant of the same species.

3. An isolated nucleotide sequence comprising an antisense sequence of SEQ ID NO: 1 operably linked to a promoter, wherein the expression of the nucleotide sequence in a plant causes seeds of the plant to have a lighter color compared to seeds of a wild-type or non-transgenic plant of the same species.

4. A DNA expression cassette comprises the nucleotide sequence of claim 1 operably linked to a promoter.

5. A DNA construct comprising a vector, wherein the vector comprises an antisense nucleotide sequence of SEQ ID NO: 1 operably linked to a promoter.

6. The construct according to claim 5, wherein the promoter is selected from the group consisting of: constitutive promoter, an inducible promoter, and an organ specific promoter.

7. A plant cell transformed with the construct according to claim 5.

8. A transgenic plant regenerated from the plant cell of claim 7, wherein the expression of the nucleotide sequence in the plant causes seeds of the plant to have a lighter color compared to seeds of a wild-type or non-transgenic plant of the same species.

9. The transgenic plant according to claim 8, wherein the transgenic plant is a cruciferous plant.

10. The transgenic plant according to claim 8, wherein the transgenic plant is of the genus *Brassica*.

11. A transgenic seed with reduced fiber content obtained from a transgenic plant, the method comprising:

(a) transforming a plant cell with the construct of claim 5;

(b) regenerating a transgenic plant from the plant cell of (a);

(c) obtain a seed from the transgenic plant of (b), wherein said seed contains said DNA construct;

and wherein expression of the nucleotide sequence reduces the fiber content in said seed compared to an untransformed seed of the same species.

* * * * *

UNITED STATES PATENT AND TRADEMARK OFFICE
CERTIFICATE OF CORRECTION

PATENT NO. : 7,429,693 B2  Page 1 of 1
APPLICATION NO. : 10/470264
DATED : September 30, 2008
INVENTOR(S) : Zheng et al.

It is certified that error appears in the above-identified patent and that said Letters Patent is hereby corrected as shown below:

On the title page:
In ITEM (22)
    1st column,      change "Filed: May 11, 2005" to -- PCT Filed: Feb. 6, 2002 --

In ITEM (60) "Related U.S. Application Data"
    1st column,      Add -- Provisional application No. 60/266,875, filed on Feb. 7, 2001 --

In ITEM (86)
    1st column,      Add -- PCT No.: PCT/CA02/00141 --

In ITEM (86)
    1st column,      Add -- § 371 (c)(1), (2), (4) date: May 11, 2005 --

In ITEM (87)
    1st column,      Add -- PCT. Pub. No.: WO02/063018 --

In ITEM (87)
    1st column,      Add -- PCT Pub Date: Aug. 15, 2002 --

Signed and Sealed this

Fifteenth Day of December, 2009

David J. Kappos
*Director of the United States Patent and Trademark Office*